US012810992B2

(12) United States Patent
Valiyambath et al.

(10) Patent No.: US 12,810,992 B2
(45) Date of Patent: Nov. 24, 2026

(54) SYSTEMS AND METHODS FOR SLEEP TRAINING

(71) Applicant: ResMed Digital Health Inc., San Diego, CA (US)

(72) Inventors: Mohankumar Krishnan Valiyambath, Singapore (SG); Liam Holley, Sydney (AU); Andrew Berry, Sydney (AU); Monica Singireddy, Sydney (AU); Aoibhe Jacqueline Turner-Heaney, Dublin (IE); Cindy Ann Chen, San Diego, CA (US); Dylan Hermes da Fonseca Beadle, Dublin (IE); Michael Scannell, Dublin (IE); David Frederick Conrad, Halifax (CA); Amar Kohli, Halifax (CA); Yuen Sang Ho, San Diego, CA (US); Mark Thomas Felcansmith, San Diego, CA (US)

(73) Assignee: ResMed Digital Health Inc., San Diego, CA (US)

( * ) Notice: Subject to any disclaimer, the term of this patent is extended or adjusted under 35 U.S.C. 154(b) by 284 days.

(21) Appl. No.: 18/589,393

(22) Filed: Feb. 27, 2024

(65) Prior Publication Data

US 2024/0290466 A1 Aug. 29, 2024

Related U.S. Application Data

(60) Provisional application No. 63/487,524, filed on Feb. 28, 2023.

(51) Int. Cl.

*G16H 20/70* (2018.01)
*A61B 5/00* (2006.01)

(Continued)

(52) U.S. Cl.

CPC ........... *G16H 20/70* (2018.01); *A61B 5/4812* (2013.01); *A61B 5/4815* (2013.01); *A61M 21/02* (2013.01); *G16H 50/70* (2018.01)

(58) Field of Classification Search

CPC ..... A61B 5/486; A61B 5/7405; A61B 5/4812; A61B 5/4815; A61B 5/1116; A61B 5/4836; A61B 5/11; A61M 21/02

See application file for complete search history.

(56) References Cited

U.S. PATENT DOCUMENTS 9,358,353 B2 6/2016 Armitstead et al.
10,328,219 B2 6/2019 Rao et al.

(Continued)

FOREIGN PATENT DOCUMENTS

WO 2008138040 A1 11/2008
WO 2012012835 A2 2/2012

(Continued)

OTHER PUBLICATIONS

Neftci, E.O., Averbeck, B.B. Reinforcement learning in artificial and biological systems. Nat Mach Intell 1, 133-143 (2019). https://doi.org/10.1038/s42256-019-0025-4 (Year: 2019).*

*Primary Examiner* — Benjamin J Klein
*Assistant Examiner* — Daniel Tehrani
(74) *Attorney, Agent, or Firm* — Nixon Peabody LLP

(57) ABSTRACT

A method for sleep training includes recommending a default sleep pattern for a user based, at least in part, on crowd-sourced sleep data. The method further includes determining first sleep quality data for the user during one or more first sleep sessions subsequent to the recommending the default sleep pattern and with the user adopting the default sleep pattern in the one or more first sleep sessions. The method further includes identifying based, at least in part, on the first sleep quality data an optimum sleep pattern for the user. The method further includes providing direction (Continued)

to the user prior to, during, or any combination thereof one or more second sleep sessions to encourage the user to sleep in the optimum sleep pattern. The method also includes presenting a dashboard for the user that communicates how the optimum sleep pattern and the providing the direction have affected sleep.

20 Claims, 10 Drawing Sheets

(51) Int. Cl.

| | |
|---|---|
| ***A61M 21/02*** | (2006.01) |
| ***G16H 50/70*** | (2018.01) |

(56) References Cited

U.S. PATENT DOCUMENTS

2008/0308112 A1* 12/2008 Aarts ................ A61M 16/0066 128/848
2009/0007922 A1* 1/2009 Harrington ............... A61F 2/00 128/859
2011/0295083 A1* 12/2011 Doelling .................. A61B 5/11 600/407
2014/0088373 A1 3/2014 Phillips et al.
2016/0007914 A1* 1/2016 Xu ........................ A61B 5/7455 600/534
2016/0073935 A1* 3/2016 van Beest ............ A61B 5/1116 600/595
2017/0311879 A1 11/2017 Armitstead et al.
2019/0371197 A1* 12/2019 Arnold .................. G06F 3/0481
2020/0261020 A1* 8/2020 Levendowski ...... A61B 5/6822
2020/0383580 A1 12/2020 Shouldice et al.
2021/0169417 A1* 6/2021 Burton ................. A61B 5/4815
2022/0007965 A1 1/2022 Tiron et al.

FOREIGN PATENT DOCUMENTS

WO 2014047310 A1 3/2014
WO 2016061629 A1 4/2016
WO 2017132726 A1 8/2017
WO 2018050913 A1 3/2018
WO 2019122413 A1 6/2019
WO 2019122414 A1 6/2019
WO 2020104465 A2 5/2020
WO WO-2021021835 A1 * 2/2021 ............. A61B 5/087
WO WO-2021220247 A1 * 11/2021 .......... A61M 16/026

* cited by examiner

SYSTEMS AND METHODS FOR SLEEP TRAINING

CROSS-REFERENCE TO RELATED APPLICATIONS

This application claims the benefit of, and priority to, U.S. Provisional Patent Application No. 63/487,524, filed Feb. 28, 2023, which is hereby incorporated by reference herein in its entirety.

TECHNICAL FIELD

The present disclosure relates generally to systems and methods for sleep training, and more particularly, to systems and methods for providing direction to a user to encourage an optimum sleep pattern.

BACKGROUND

Many individuals suffer from sleep-related and/or respiratory-related disorders such as, for example, Sleep Disordered Breathing (SDB), which can include Obstructive Sleep Apnea (OSA), Central Sleep Apnea (CSA), other types of apneas such as mixed apneas and hypopneas, Respiratory Effort Related Arousal (RERA), and snoring. In some cases, these disorders manifest, or manifest more pronouncedly, when the individual is in a particular lying/sleeping position. Such positional sleep apnea is very prevalent and could lead to therapy not treating the patient appropriately. Further, people may fall asleep in the position they think is the most comfortable; however, this may lead to inefficient sleep or sleep that is not optimal. Accordingly, needs exist for systems and methods for training someone to be in a particular lying/sleeping pattern or position to eliminate or reduce sleep-related and/or respiratory-related disorders.

The present disclosure is directed to solving these and other problems.

SUMMARY

According to some implementations of the present disclosure, a method includes recommending a default sleep pattern for a user based, at least in part, on crowd-sourced sleep data. The method also includes determining first sleep quality data for the user during one or more first sleep sessions subsequent to the recommending the default sleep pattern and with the user adopting the default sleep pattern in the one or more first sleep sessions. The method also includes identifying based, at least in part, on the first sleep quality data an optimum sleep pattern for the user. The method also includes providing direction to the user prior to, during, or any combination thereof one or more second sleep sessions to encourage the user to sleep in the optimum sleep pattern. The method also includes presenting a dashboard for the user that communicates how the optimum sleep pattern and the providing the direction have affected sleep.

Aspects of the method include the direction being based on an algorithm generated from crowd-sourced direction information. According to this aspect, the method further includes applying reinforcement learning to the algorithm for personalizing the direction specific to the user. Aspects of the method include the reinforcement learning being based, at least in part, on which direction is determined to prevent or reduce sleep disordered breathing by the user based on second sleep quality data for the user during the one or more second sleep sessions. Aspects of the method include the reinforcement learning being based, at least in part, on which direction is determined to not wake the user, a bed partner of the user, or any combination thereof. Aspects of the method include the first sleep quality data correlating historical sleep positions of the user with historical sleep events of the user related to a quality of sleep. Aspects of the method include the historical sleep events including an amount and a type of movement, a total amount sleep, an amount of REM sleep, an amount of deep sleep, an amount of light sleep, a length of time to fall asleep, a number of sleep interruptions, an amount of snoring, a number of apnea events, a measure of blood oxygen saturation, or any combination thereof. Aspects of the method include the default sleep pattern being determined based on a common sleep pattern among one or more crowd-sourced users associated with the crowd-sourced sleep data who share one or more demographic, medical or physiological traits, or any combination thereof, with the user. Aspects of the method include presenting information on the dashboard regarding which sleep position, sleep pattern, or any combination thereof provides a fewest number of sleep disordered breathing events. Aspects of the method include the direction being one or more mechanical stimulations, one or more aural stimulations, one or more olfactory stimulations, or any combination thereof provided to the user effected, at least in part, by one or more devices associated with the user, one or more devices associated with a bed of the user, one or more devices located in an environment of the user, or any combination thereof. Further aspects include at least one device of the one or more devices associated with the user being a wearable device configured to include specific vibration patterns, with each specific vibration pattern related to a specific sleep position. Aspects of the method include the optimum sleep pattern being identified based, at least in part, on feedback from the user. Further aspects include the feedback providing information on presence of a bed partner, a weather event, a change in one or more medications, use of a drug, use of alcohol, energy level after sleep session, soreness during or after sleep session, or any combination thereof. Aspects of the method include the default sleep pattern being a default sleep position, a default initial position, a default predetermined position which the user should maintain for a predetermined period of sleep, or a combination of positions during sleep. Aspects of the method include the optimum sleep pattern being an optimum sleep position, an optimum initial position, an optimum predetermined position which the user should maintain for a predetermined period of sleep, or a combination of positions during sleep. Aspects of the method include the direction including instructions to use a device to encourage a certain sleep position.

According to some implementations of the present disclosure, a system includes a memory and a control system. The memory stores machine-readable instructions. The control system includes one or more processors configured to execute the machine-readable instructions to recommend a default sleep pattern for a user based, at least in part, on crowd-sourced sleep data. The one or more processors further are configured to execute the machine-readable instructions to determine first sleep quality data for the user during one or more first sleep sessions subsequent to the recommending the default sleep pattern and with the user adopting the default sleep pattern in the one or more first sleep sessions. The one or more processors further are configured to execute the machine-readable instructions to identify based, at least in part, on the first sleep quality data an optimum sleep pattern for the user. The one or more processors further are configured to execute the machine-readable instructions to provide direction to the user prior to, during, or any combination thereof one or more second sleep sessions to encourage the user to sleep in the optimum sleep pattern. The one or more processors further are configured to execute the machine-readable instructions to present a dashboard for the user that communicates how the optimum sleep pattern and the providing the direction have affected sleep.

The above summary is not intended to represent each implementation or every aspect of the present disclosure. Additional features and benefits of the present disclosure are apparent from the detailed description and figures set forth below.

Figure 1:
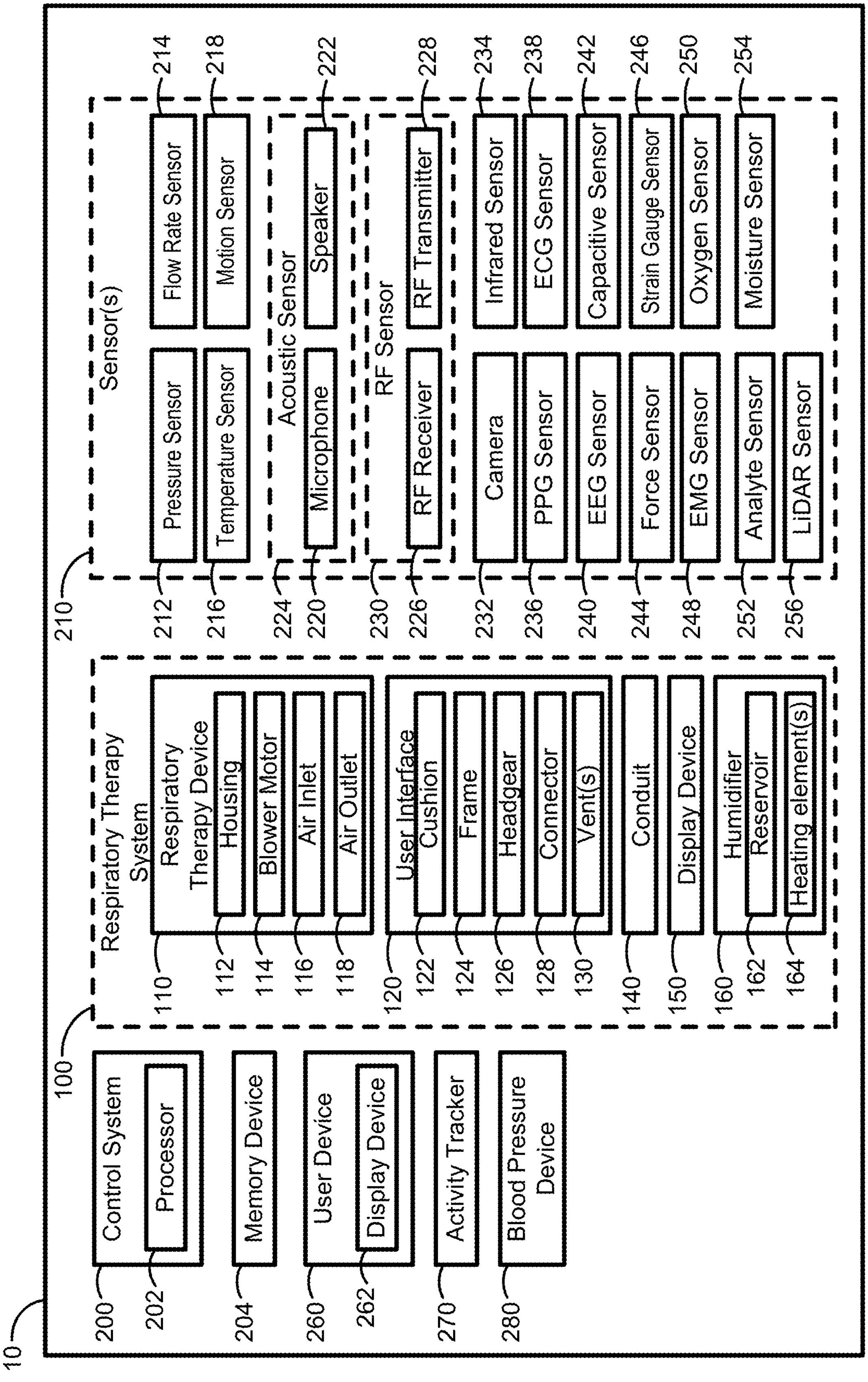
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The present disclosure provides systems and methods for training a user to sleep in an optimum sleep pattern during sleep to prevent/reduce OSA. The methods and systems aim to help the user select a sleeping position that gives the user the most optimum sleep quality, while potentially also alleviating additional events, such as sleep disordered breathing events, to help them get a better night of sleep. Multiple positions could be given based on user feedback/input to adjust recommendations in case the user is injured (or sore in specific location(s)). Aspects involve providing direction to the user, such as through stimulation(s) and/or instruction(s) with the least amount of intrusion to the user, to a bed partner associated with the user, or any combination thereof. Further aspects include application of reinforcement learning to prevent or reduce OSA. Devices within the environment of the user can be controlled, such as through machine learning algorithms, to trigger movement during sleep prior to or when OSA is indicated so that the user is encouraged to move sleeping positions. Such control over devices can be determined from a patient population and, as described above, thereafter have reinforcement learning applied to personalize triggers for the patient through (i) learning which triggers are most effective in preventing or reducing OSA; (ii) learning which triggers are least likely to wake the patient or partner; (iii) augment movement devices to improve their effect on OSA; (iv) balance sleep comfort over correct sleep position, such as by letting a user be despite the user not being in the correct position (e.g., low AHI); (v) take into consideration the user being with a bed partner, or any combination thereof. The disclosed methods and devices also provide a dashboard that visually guides the user through the process of sleep training in an effort to make the user invested in the process.

The methods and systems can include device(s) to monitor asleep/awake state; trigger movement; detect user position (which may be the same or different devices that trigger movement); and to detect constriction of the airway indicating potential sleep apnea. As described further below, aspects for trigging movement can include introducing auditory or mechanical or olfactory or any other sensory stimulants from a PAP device, wearables (intensity of vibration/sound), or any device within the environment of the user that can change the user's sleeping position (e.g., selectively inflatable pillow or airbed). Further, machine learning can be used to learn a user's individual responses to different positions as well as stimuli and also relative sleep comfort arising from the different positions and personalizing the treatment. Such personalization can balance sleep comfort with correct sleep position, along with other competing factors.

Indeed, many individuals suffer from sleep-related and/or respiratory disorders, such as Sleep Disordered Breathing (SDB) such as Obstructive Sleep Apnea (OSA), Central Sleep Apnea (CSA) and other types of apneas, Respiratory Effort Related Arousal (RERA), snoring, Cheyne-Stokes Respiration (CSR), respiratory insufficiency, Obesity Hyperventilation Syndrome (OHS), Chronic Obstructive Pulmonary Disease (COPD), Periodic Limb Movement Disorder (PLMD), Restless Leg Syndrome (RLS), Neuromuscular Disease (NMD), and chest wall disorders.

Obstructive Sleep Apnea (OSA), a form of Sleep Disordered Breathing (SDB), is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). CSA results when the brain temporarily stops sending signals to the muscles that control breathing. Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for ten seconds or longer leading to arousal from sleep and which does not fulfill the criteria for an apnea or hypopnea event. RERAs are defined as a sequence of breaths characterized by increasing respiratory effort leading to an arousal from sleep, but which does not meet criteria for an apnea or hypopnea. These events fulfil the following criteria: (1) a pattern of progressively more negative esophageal pressure, terminated by a sudden change in pressure to a less negative level and an arousal, and (2) the event lasts ten seconds or longer. In some implementations, a Nasal Cannula/Pressure Transducer System is adequate and reliable in the detection of RERAs. A RERA detector may be based on a real flow signal derived from a respiratory therapy device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358,353, assigned to ResMed Ltd., the disclosure of each of which is hereby incorporated by reference herein in their entireties.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung. COPD encompasses a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 10, according to some implementations of the present disclosure, is illustrated. The system 10 includes a respiratory therapy system 100, a control system 200, one or more sensors 210, a user device 260, and an activity tracker 270.

The respiratory therapy system 100 includes a respiratory pressure therapy (RPT) device 110 (referred to herein as respiratory therapy device 110), a user interface 120 (also referred to as a mask or a patient interface), a conduit 140 (also referred to as a tube or an air circuit), a display device 150, and a humidifier 160. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 100 is generally used to treat individuals suffering from one or more sleep-related respiratory disorders (e.g., obstructive sleep apnea, central sleep apnea, or mixed sleep apnea).

The respiratory therapy system 100 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Figure 2:
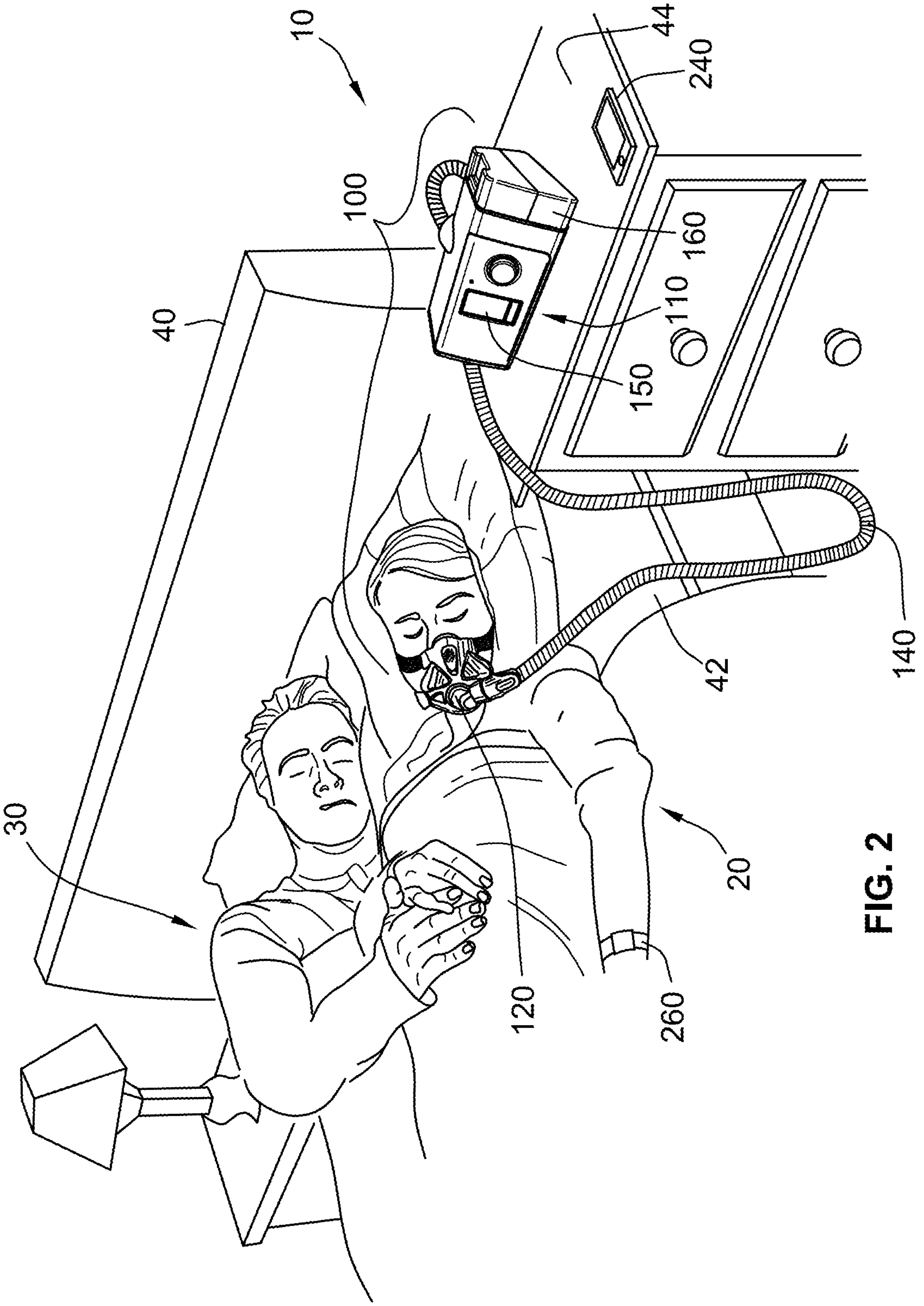
FIG. 2 is a perspective view of at least a portion of the system of FIG. 1, a user, and a bed partner, according to some implementations of the present disclosure.

As shown in FIG. 2, the respiratory therapy system 100 can be used to treat user 20. In this example, the user 20 of the respiratory therapy system 100 and a bed partner 30 are located in a bed 40 and are laying on a mattress 42. The user interface 120 can be worn by the user 20 during a sleep session. The respiratory therapy system 100 generally aids in increasing the air pressure in the throat of the user 20 to aid in preventing the airway from closing and/or narrowing during sleep. The respiratory therapy device 110 can be positioned on a nightstand 44 that is directly adjacent to the bed 40 as shown in FIG. 2, or more generally, on any surface or structure that is generally adjacent to the bed 40 and/or the user 20.

The respiratory therapy device 110 is generally used to generate pressurized air that is delivered to a user (e.g., using one or more motors that drive one or more compressors). In some implementations, the respiratory therapy device 110 generates continuous constant air pressure that is delivered to the user. In other implementations, the respiratory therapy device 110 generates two or more predetermined pressures (e.g., a first predetermined air pressure and a second predetermined air pressure). In still other implementations, the respiratory therapy device 110 generates a variety of different air pressures within a predetermined range. For example, the respiratory therapy device 110 can deliver at least about 6 $cmH_2O$, at least about 10 $cmH_2O$, at least about 20 $cmH_2O$, between about 6 $cmH_2O$ and about 10 $cmH_2O$, between about 7 $cmH_2O$ and about 12 $cmH_2O$, etc. The respiratory therapy device 110 can also deliver pressurized air at a predetermined flow rate between, for example, about −20 L/min and about 150 L/min, while maintaining a positive pressure (relative to the ambient pressure).

Figure 3A:
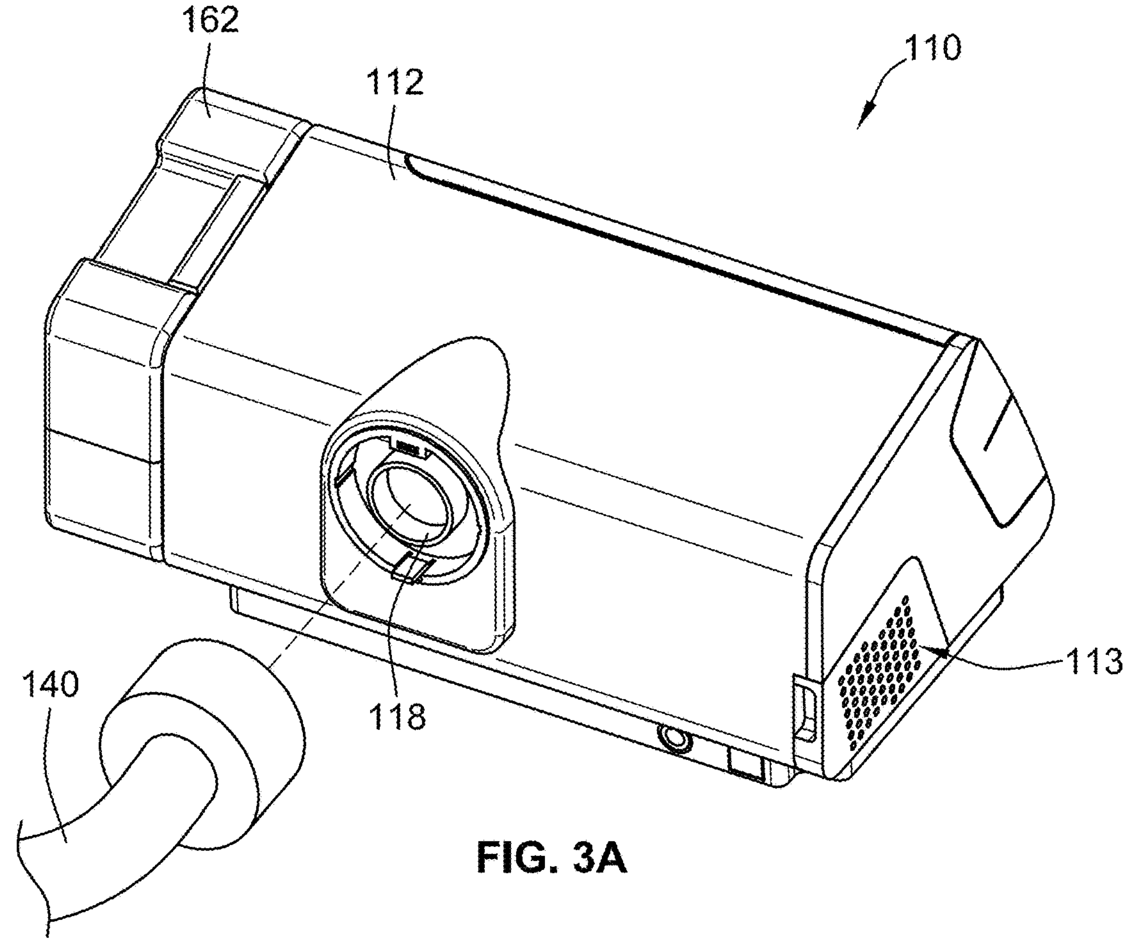
FIG. 3A is a perspective view of a respiratory therapy device of the system of FIG. 1, according to some implementations of the present disclosure.
Figure 3B:
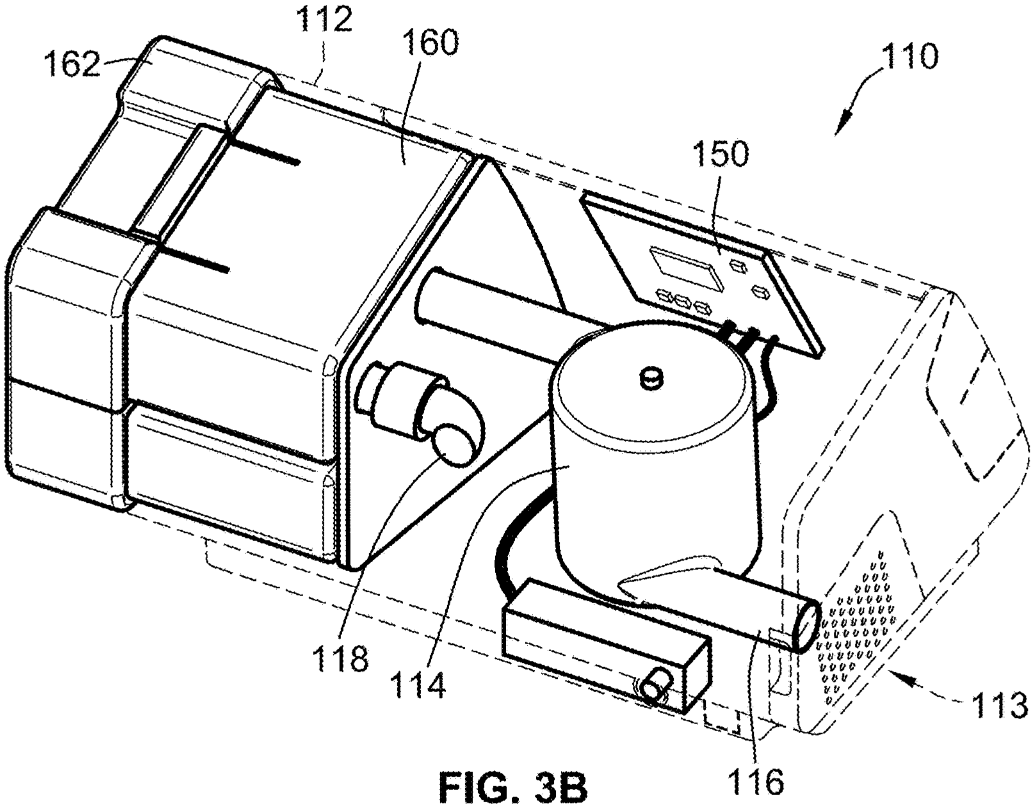
FIG. 3B is a perspective view of the respiratory therapy device of FIG. 3A illustrating an interior of a housing, according to some implementations of the present disclosure.

The respiratory therapy device 110 includes a housing 112, a blower motor 114, an air inlet 116, and an air outlet 118 (FIG. 1). Referring to FIGS. 3A and 3B, the blower motor 114 is at least partially disposed or integrated within the housing 112. The blower motor 114 draws air from outside the housing 112 (e.g., atmosphere) via the air inlet 116 and causes pressurized air to flow through the humidifier 160, and through the air outlet 118. In some implementations, the air inlet 116 and/or the air outlet 118 include a cover that is moveable between a closed position and an open position (e.g., to prevent or inhibit air from flowing through the air inlet 116 or the air outlet 118). As shown in FIGS. 3A and 3B, the housing 112 can include a vent 113 to allow air to pass through the housing 112 to the air inlet 116. As described below, the conduit 140 is coupled to the air outlet 118 of the respiratory therapy device 110.

Referring back to FIG. 1, the user interface 120 engages a portion of the user's face and delivers pressurized air from the respiratory therapy device 110 to the user's airway to aid in preventing the airway from narrowing and/or collapsing during sleep. This may also increase the user's oxygen intake during sleep. Generally, the user interface 120 engages the user's face such that the pressurized air is delivered to the user's airway via the user's mouth, the user's nose, or both the user's mouth and nose. Together, the respiratory therapy device 110, the user interface 120, and the conduit 140 form an air pathway fluidly coupled with an airway of the user. The pressurized air also increases the user's oxygen intake during sleep. Depending upon the therapy to be applied, the user interface 120 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 $cmH_2O$.

The user interface 120 can include, for example, a cushion 122, a frame 124, a headgear 126, connector 128, and one or more vents 130. The cushion 122 and the frame 124 define a volume of space around the mouth and/or nose of the user. When the respiratory therapy system 100 is in use, this volume space receives pressurized air (e.g., from the respiratory therapy device 110 via the conduit 140) for passage into the airway(s) of the user. The headgear 126 is generally used to aid in positioning and/or stabilizing the user interface 120 on a portion of the user (e.g., the face), and along with the cushion 122 (which, for example, can comprise silicone, plastic, foam, etc.) aids in providing a substantially air-tight seal between the user interface 120 and the user 20. In some implementations the headgear 126 includes one or more straps (e.g., including hook and loop fasteners). The connector 128 is generally used to couple (e.g., connect and fluidly couple) the conduit 140 to the cushion 122 and/or frame 124. Alternatively, the conduit 140 can be directly coupled to the cushion 122 and/or frame 124 without the connector 128. The vent 130 can be used for permitting the escape of carbon dioxide and other gases exhaled by the user 20. The user interface 120 generally can include any suitable number of vents (e.g., one, two, five, ten, etc.).

As shown in FIG. 2, in some implementations, the user interface 120 is a facial mask (e.g., a full face mask) that covers at least a portion of the nose and mouth of the user 20. Alternatively, the user interface 120 can be a nasal mask that provides air to the nose of the user or a nasal pillow mask that delivers air directly to the nostrils of the user 20. In other implementations, the user interface 120 includes a mouthpiece (e.g., a night guard mouthpiece molded to conform to the teeth of the user, a mandibular repositioning device, etc.).

Referring back to FIG. 1, the conduit 140 (also referred to as an air circuit or tube) allows the flow of air between components of the respiratory therapy system 100, such as between the respiratory therapy device 110 and the user interface 120. In some implementations, there can be separate limbs of the conduit for inhalation and exhalation. In other implementations, a single limb conduit is used for both inhalation and exhalation.

Referring to FIG. 3A, the conduit 140 includes a first end 142 that is coupled to the air outlet 118 of the respiratory therapy device 110. The first end 142 can be coupled to the air outlet 118 of the respiratory therapy device 110 using a variety of techniques (e.g., a press fit connection, a snap fit connection, a threaded connection, etc.). In some implementations, the conduit 140 includes one or more heating elements that heat the pressurized air flowing through the conduit 140 (e.g., heat the air to a predetermined temperature or within a range of predetermined temperatures). Such heating elements can be coupled to and/or imbedded in the conduit 140. In such implementations, the first end 142 can include an electrical contact that is electrically coupled to the respiratory therapy device 110 to power the one or more heating elements of the conduit 140. For example, the electrical contact can be electrically coupled to an electrical contact of the air outlet 118 of the respiratory therapy device 110. In this example, electrical contact of the conduit 140 can be a male connector and the electrical contact of the air outlet 118 can be female connector, or, alternatively, the opposite configuration can be used.

The display device 150 is generally used to display image(s) including still images, video images, or both and/or information regarding the respiratory therapy device 110. For example, the display device 150 can provide information regarding the status of the respiratory therapy device 110 (e.g., whether the respiratory therapy device 110 is on/off, the pressure of the air being delivered by the respiratory therapy device 110, the temperature of the air being delivered by the respiratory therapy device 110, etc.) and/or other information (e.g., a sleep score and/or a therapy score, also referred to as a myAir™ score, such as described in WO 2016/061629 and U.S. Patent Pub. No. 2017/0311879, which are hereby incorporated by reference herein in their entireties, the current date/time, personal information for the user 20, etc.). In some implementations, the display device 150 acts as a human-machine interface (HMI) that includes a graphic user interface (GUI) configured to display the image(s) as an input interface. The display device 150 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 110.

The humidifier 160 is coupled to or integrated in the respiratory therapy device 110 and includes a reservoir 162 for storing water that can be used to humidify the pressurized air delivered from the respiratory therapy device 110. The humidifier 160 includes a one or more heating elements 164 to heat the water in the reservoir to generate water vapor. The humidifier 160 can be fluidly coupled to a water vapor inlet of the air pathway between the blower motor 114 and the air outlet 118, or can be formed in-line with the air pathway between the blower motor 114 and the air outlet 118. For example, as shown in FIG. 3, air flow from the air inlet 116 through the blower motor 114, and then through the humidifier 160 before exiting the respiratory therapy device 110 via the air outlet 118.

While the respiratory therapy system 100 has been described herein as including each of the respiratory therapy device 110, the user interface 120, the conduit 140, the display device 150, and the humidifier 160, more or fewer components can be included in a respiratory therapy system according to implementations of the present disclosure. For example, a first alternative respiratory therapy system includes the respiratory therapy device 110, the user interface 120, and the conduit 140. As another example, a second alternative system includes the respiratory therapy device 110, the user interface 120, and the conduit 140, and the display device 150. Thus, various respiratory therapy systems can be formed using any portion or portions of the components shown and described herein and/or in combination with one or more other components.

The control system 200 includes one or more processors 202 (hereinafter, processor 202). The control system 200 is generally used to control (e.g., actuate) the various components of the system 10 and/or analyze data obtained and/or generated by the components of the system 10. The processor 202 can be a general or special purpose processor or microprocessor. While one processor 202 is illustrated in FIG. 1, the control system 200 can include any number of processors (e.g., one processor, two processors, five processors, ten processors, etc.) that can be in a single housing, or located remotely from each other. The control system 200 (or any other control system) or a portion of the control system 200 such as the processor 202 (or any other processor(s) or portion(s) of any other control system), can be used to carry out one or more steps of any of the methods described and/or claimed herein. The control system 200 can be coupled to and/or positioned within, for example, a housing of the user device 260, a portion (e.g., the respiratory therapy device 110) of the respiratory therapy system 100, and/or within a housing of one or more of the sensors 210. The control system 200 can be centralized (within one such housing) or decentralized (within two or more of such housings, which are physically distinct). In such implementations including two or more housings containing the control system 200, the housings can be located proximately and/or remotely from each other.

The memory device 204 stores machine-readable instructions that are executable by the processor 202 of the control system 200. The memory device 204 can be any suitable computer readable storage device or media, such as, for example, a random or serial access memory device, a hard drive, a solid state drive, a flash memory device, etc. While one memory device 204 is shown in FIG. 1, the system 10 can include any suitable number of memory devices 204 (e.g., one memory device, two memory devices, five memory devices, ten memory devices, etc.). The memory device 204 can be coupled to and/or positioned within a housing of a respiratory therapy device 110 of the respiratory therapy system 100, within a housing of the user device 260, within a housing of one or more of the sensors 210, or any combination thereof. Like the control system 200, the memory device 204 can be centralized (within one such housing) or decentralized (within two or more of such housings, which are physically distinct).

In some implementations, the memory device 204 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a geographic location of the user, a relationship status, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

As described herein, the processor 202 and/or memory device 204 can receive data (e.g., physiological data and/or audio data) from the one or more sensors 210 such that the data for storage in the memory device 204 and/or for analysis by the processor 202. The processor 202 and/or memory device 204 can communicate with the one or more sensors 210 using a wired connection or a wireless connection (e.g., using an RF communication protocol, a Wi-Fi communication protocol, a Bluetooth communication protocol, over a cellular network, etc.). In some implementations, the system 10 can include an antenna, a receiver (e.g., an RF receiver), a transmitter (e.g., an RF transmitter), a transceiver, or any combination thereof. Such components can be coupled to or integrated a housing of the control system 200 (e.g., in the same housing as the processor 202 and/or memory device 204), or the user device 260.

Referring to back to FIG. 1, the one or more sensors 210 include a pressure sensor 212, a flow rate sensor 214, temperature sensor 216, a motion sensor 218, a microphone 220, a speaker 222, a radio-frequency (RF) receiver 226, a RF transmitter 228, a camera 232, an infrared sensor 234, a photoplethysmogram (PPG) sensor 236, an electrocardiogram (ECG) sensor 238, an electroencephalography (EEG) sensor 240, a capacitive sensor 242, a force sensor 244, a strain gauge sensor 246, an electromyography (EMG) sensor 248, an oxygen sensor 250, an analyte sensor 252, a moisture sensor 254, a LiDAR sensor 256, or any combination thereof. Generally, each of the one or more sensors 210 are configured to output sensor data that is received and stored in the memory device 204 or one or more other memory devices.

While the one or more sensors 210 are shown and described as including each of the pressure sensor 212, the flow rate sensor 214, the temperature sensor 216, the motion sensor 218, the microphone 220, the speaker 222, the RF receiver 226, the RF transmitter 228, the camera 232, the infrared sensor 234, the photoplethysmogram (PPG) sensor 236, the electrocardiogram (ECG) sensor 238, the electroencephalography (EEG) sensor 240, the capacitive sensor 242, the force sensor 244, the strain gauge sensor 246, the electromyography (EMG) sensor 248, the oxygen sensor 250, the analyte sensor 252, the moisture sensor 254, and the LiDAR sensor 256, more generally, the one or more sensors 210 can include any combination and any number of each of the sensors described and/or shown herein.

As described herein, the system 10 generally can be used to generate physiological data associated with a user (e.g., a user of the respiratory therapy system 100) during a sleep session. The physiological data can be analyzed to generate one or more sleep-related parameters, which can include any parameter, measurement, etc. related to the user during the sleep session. The one or more sleep-related parameters that can be determined for the user 20 during the sleep session include, for example, an Apnea-Hypopnea Index (AHI) score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory therapy device 110, a heart rate, a heart rate variability, movement of the user 20, temperature, EEG activity, EMG activity, arousal, snoring, choking, coughing, whistling, wheezing, or any combination thereof.

The one or more sensors 210 can be used to generate, for example, physiological data, audio data, or both. Physiological data generated by one or more of the sensors 210 can be used by the control system 200 to determine a sleep-wake signal associated with the user 20 (FIG. 2) during the sleep session and one or more sleep-related parameters. The sleep-wake signal can be indicative of one or more sleep states, including wakefulness, relaxed wakefulness, micro-awakenings, or distinct sleep stages such as, for example, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more sensors, such as the one or more sensors 210, are described in, for example, WO 2014/047310, U.S. Patent Pub. No. 2014/0088373, WO 2017/132726, WO 2019/122413, WO 2019/122414, and U.S. Patent Pub. No. 2020/0383580 each of which is hereby incorporated by reference herein in its entirety.

In some implementations, the sleep-wake signal described herein can be timestamped to indicate a time that the user enters the bed, a time that the user exits the bed, a time that the user attempts to fall asleep, etc. The sleep-wake signal can be measured by the one or more sensors 210 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 110, or any combination thereof during the sleep session. The event(s) can include snoring, apneas, central apneas, obstructive apneas, mixed apneas, hypopneas, a mask leak (e.g., from the user interface 120), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, the physiological data and/or the sleep-related parameters can be analyzed to determine one or more sleep-related scores.

Physiological data and/or audio data generated by the one or more sensors 210 can also be used to determine a respiration signal associated with a user during a sleep session. The respiration signal is generally indicative of respiration or breathing of the user during the sleep session. The respiration signal can be indicative of and/or analyzed to determine (e.g., using the control system 200) one or more sleep-related parameters, such as, for example, a respiration rate, a respiration rate variability, an inspiration amplitude, an expiration amplitude, an inspiration-expiration ratio, an occurrence of one or more events, a number of events per hour, a pattern of events, a sleep state, a sleet stage, an apnea-hypopnea index (AHI), pressure settings of the respiratory therapy device 110, or any combination thereof. The one or more events can include snoring, apneas, central apneas, obstructive apneas, mixed apneas, hypopneas, a mask leak (e.g., from the user interface 120), a cough, a restless leg, a sleeping disorder, choking, an increased heart rate, labored breathing, an asthma attack, an epileptic episode, a seizure, increased blood pressure, or any combination thereof. Many of the described sleep-related parameters are physiological parameters, although some of the sleep-related parameters can be considered to be non-physiological parameters. Other types of physiological and/or non-physiological parameters can also be determined, either from the data from the one or more sensors 210, or from other types of data.

The pressure sensor 212 outputs pressure data that can be stored in the memory device 204 and/or analyzed by the processor 202 of the control system 200. In some implementations, the pressure sensor 212 is an air pressure sensor (e.g., barometric pressure sensor) that generates sensor data indicative of the respiration (e.g., inhaling and/or exhaling) of the user of the respiratory therapy system 100 and/or ambient pressure. In such implementations, the pressure sensor 212 can be coupled to or integrated in the respiratory therapy device 110. The pressure sensor 212 can be, for example, a capacitive sensor, an electromagnetic sensor, a piezoelectric sensor, a strain-gauge sensor, an optical sensor, a potentiometric sensor, or any combination thereof.

The flow rate sensor 214 outputs flow rate data that can be stored in the memory device 204 and/or analyzed by the processor 202 of the control system 200. Examples of flow rate sensors (such as, for example, the flow rate sensor 214) are described in International Publication No. WO 2012/012835 and U.S. Pat. No. 10,328,219, both of which are hereby incorporated by reference herein in their entireties. In some implementations, the flow rate sensor 214 is used to determine an air flow rate from the respiratory therapy device 110, an air flow rate through the conduit 140, an air flow rate through the user interface 120, or any combination thereof. In such implementations, the flow rate sensor 214 can be coupled to or integrated in the respiratory therapy device 110, the user interface 120, or the conduit 140. The flow rate sensor 214 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some implementations, the flow rate sensor 214 is configured to measure a vent flow (e.g., intentional "leak"), an unintentional leak (e.g., mouth leak and/or mask leak), a patient flow (e.g., air into and/or out of lungs), or any combination thereof. In some implementations, the flow rate data can be analyzed to determine cardiogenic oscillations of the user. In some examples, the pressure sensor 212 can be used to determine a blood pressure of a user.

The temperature sensor 216 outputs temperature data that can be stored in the memory device 204 and/or analyzed by the processor 202 of the control system 200. In some implementations, the temperature sensor 216 generates temperatures data indicative of a core body temperature of the user 20 (FIG. 2), a skin temperature of the user 20, a temperature of the air flowing from the respiratory therapy device 110 and/or through the conduit 140, a temperature in the user interface 120, an ambient temperature, or any combination thereof. The temperature sensor 216 can be, for example, a thermocouple sensor, a thermistor sensor, a silicon band gap temperature sensor or semiconductor-based sensor, a resistance temperature detector, or any combination thereof.

The motion sensor 218 outputs motion data that can be stored in the memory device 204 and/or analyzed by the processor 202 of the control system 200. The motion sensor 218 can be used to detect movement of the user 20 during the sleep session, and/or detect movement of any of the components of the respiratory therapy system 100, such as the respiratory therapy device 110, the user interface 120, or the conduit 140. The motion sensor 218 can include one or more inertial sensors, such as accelerometers, gyroscopes, and magnetometers. In some implementations, the motion sensor 218 alternatively or additionally generates one or more signals representing bodily movement of the user, from which may be obtained a signal representing a sleep state of the user; for example, via a respiratory movement of the user. In some implementations, the motion data from the motion sensor 218 can be used in conjunction with additional data from another one of the sensors 210 to determine the sleep state of the user.

The microphone 220 outputs sound and/or audio data that can be stored in the memory device 204 and/or analyzed by the processor 202 of the control system 200. The audio data generated by the microphone 220 is reproducible as one or more sound(s) during a sleep session (e.g., sounds from the user 20). The audio data form the microphone 220 can also be used to identify (e.g., using the control system 200) an event experienced by the user during the sleep session, as described in further detail herein. The microphone 220 can be coupled to or integrated in the respiratory therapy device 110, the user interface 120, the conduit 140, or the user device 260. In some implementations, the system 10 includes a plurality of microphones (e.g., two or more microphones and/or an array of microphones with beamforming) such that sound data generated by each of the plurality of microphones can be used to discriminate the sound data generated by another of the plurality of microphones The speaker 222 outputs sound waves that are audible to a user of the system 10 (e.g., the user 20 of FIG. 2). The speaker 222 can be used, for example, as an alarm clock or to play an alert or message to the user 20 (e.g., in response to an event). In some implementations, the speaker 222 can be used to communicate the audio data generated by the microphone 220 to the user. The speaker 222 can be coupled to or integrated in the respiratory therapy device 110, the user interface 120, the conduit 140, or the user device 260.

The microphone 220 and the speaker 222 can be used as separate devices. In some implementations, the microphone 220 and the speaker 222 can be combined into an acoustic sensor 224 (e.g., a SONAR sensor), as described in, for example, WO 2018/050913, WO 2020/104465, U.S. Pat. App. Pub. No. 2022/0007965, each of which is hereby incorporated by reference herein in its entirety. In such implementations, the speaker 222 generates or emits sound waves at a predetermined interval and the microphone 220 detects the reflections of the emitted sound waves from the speaker 222. The sound waves generated or emitted by the speaker 222 have a frequency that is not audible to the human ear (e.g., below 20 Hz or above around 18 kHz) so as not to disturb the sleep of the user 20 or the bed partner 30 (FIG. 2). Based at least in part on the data from the microphone 220 and/or the speaker 222, the control system 200 can determine a location of the user 20 (FIG. 2) and/or one or more of the sleep-related parameters described in herein such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory therapy device 110, or any combination thereof. In such a context, a sonar sensor may be understood to concern an active acoustic sensing, such as by generating and/or transmitting ultrasound and/or low frequency ultrasound sensing signals (e.g., in a frequency range of about 17-23 kHz, 18-22 kHz, or 17-18 kHz, for example), through the air.

In some implementations, the sensors 210 include (i) a first microphone that is the same as, or similar to, the microphone 220, and is integrated in the acoustic sensor 224 and (ii) a second microphone that is the same as, or similar to, the microphone 220, but is separate and distinct from the first microphone that is integrated in the acoustic sensor 224.

The RF transmitter 228 generates and/or emits radio waves having a predetermined frequency and/or a predetermined amplitude (e.g., within a high frequency band, within a low frequency band, long wave signals, short wave signals, etc.). The RF receiver 226 detects the reflections of the radio waves emitted from the RF transmitter 228, and this data can be analyzed by the control system 200 to determine a location of the user and/or one or more of the sleep-related parameters described herein. An RF receiver (either the RF receiver 226 and the RF transmitter 228 or another RF pair) can also be used for wireless communication between the control system 200, the respiratory therapy device 110, the one or more sensors 210, the user device 260, or any combination thereof. While the RF receiver 226 and RF transmitter 228 are shown as being separate and distinct elements in FIG. 1, in some implementations, the RF receiver 226 and RF transmitter 228 are combined as a part of an RF sensor 230 (e.g. a RADAR sensor). In some such implementations, the RF sensor 230 includes a control circuit. The format of the RF communication can be Wi-Fi, Bluetooth, or the like.

In some implementations, the RF sensor 230 is a part of a mesh system. One example of a mesh system is a Wi-Fi mesh system, which can include mesh nodes, mesh router(s), and mesh gateway(s), each of which can be mobile/movable or fixed. In such implementations, the Wi- Fi mesh system includes a Wi-Fi router and/or a Wi-Fi controller and one or more satellites (e.g., access points), each of which include an RF sensor that the is the same as, or similar to, the RF sensor 230. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 232 outputs image data reproducible as one or more images (e.g., still images, video images, thermal images, or any combination thereof) that can be stored in the memory device 204. The image data from the camera 232 can be used by the control system 200 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 232 can be used to, for example, identify a location of the user, to determine chest movement of the user (FIG. 2), to determine air flow of the mouth and/or nose of the user, to determine a time when the user enters the bed (FIG. 2), and to determine a time when the user exits the bed. In some implementations, the camera 232 includes a wide angle lens or a fish eye lens.

The infrared (IR) sensor 234 outputs infrared image data reproducible as one or more infrared images (e.g., still images, video images, or both) that can be stored in the memory device 204. The infrared data from the IR sensor 234 can be used to determine one or more sleep-related parameters during a sleep session, including a temperature of the user 20 and/or movement of the user 20. The IR sensor 234 can also be used in conjunction with the camera 232 when measuring the presence, location, and/or movement of the user 20. The IR sensor 234 can detect infrared light having a wavelength between about 400 nm and about 1 mm, for example, while the camera 232 can detect visible light having a wavelength between about 380 nm and about 740 nm.

The PPG sensor 236 outputs physiological data associated with the user 20 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 236 can be worn by the user 20, embedded in clothing and/or fabric that is worn by the user 20, embedded in and/or coupled to the user interface 120 and/or its associated headgear (e.g., straps, etc.), etc.

The ECG sensor 238 outputs physiological data associated with electrical activity of the heart of the user 20. In some implementations, the ECG sensor 238 includes one or more electrodes that are positioned on or around a portion of the user 20 during the sleep session. The physiological data from the ECG sensor 238 can be used, for example, to determine one or more of the sleep-related parameters described herein.

The EEG sensor 240 outputs physiological data associated with electrical activity of the brain of the user 20. In some implementations, the EEG sensor 240 includes one or more electrodes that are positioned on or around the scalp of the user 20 during the sleep session. The physiological data from the EEG sensor 240 can be used, for example, to determine a sleep state and/or a sleep stage of the user 20 at any given time during the sleep session. In some implementations, the EEG sensor 240 can be integrated in the user interface 120 and/or the associated headgear (e.g., straps, etc.).

The capacitive sensor 242, the force sensor 244, and the strain gauge sensor 246 output data that can be stored in the memory device 204 and used/analyzed by the control system 200 to determine, for example, one or more of the sleep-related parameters described herein. The EMG sensor 248 outputs physiological data associated with electrical activity produced by one or more muscles. The oxygen sensor 250 outputs oxygen data indicative of an oxygen concentration of gas (e.g., in the conduit 140 or at the user interface 120). The oxygen sensor 250 can be, for example, an ultrasonic oxygen sensor, an electrical oxygen sensor, a chemical oxygen sensor, an optical oxygen sensor, a pulse oximeter (e.g., $SpO_2$ sensor), or any combination thereof.

The analyte sensor 252 can be used to detect the presence of an analyte in the exhaled breath of the user 20. The data output by the analyte sensor 252 can be stored in the memory device 204 and used by the control system 200 to determine the identity and concentration of any analytes in the breath of the user. In some implementations, the analyte sensor 174 is positioned near a mouth of the user to detect analytes in breath exhaled from the user's mouth. For example, when the user interface 120 is a facial mask that covers the nose and mouth of the user, the analyte sensor 252 can be positioned within the facial mask to monitor the user's mouth breathing. In other implementations, such as when the user interface 120 is a nasal mask or a nasal pillow mask, the analyte sensor 252 can be positioned near the nose of the user to detect analytes in breath exhaled through the user's nose. In still other implementations, the analyte sensor 252 can be positioned near the user's mouth when the user interface 120 is a nasal mask or a nasal pillow mask. In this implementation, the analyte sensor 252 can be used to detect whether any air is inadvertently leaking from the user's mouth and/or the user interface 120. In some implementations, the analyte sensor 252 is a volatile organic compound (VOC) sensor that can be used to detect carbon-based chemicals or compounds. In some implementations, the analyte sensor 174 can also be used to detect whether the user is breathing through their nose or mouth. For example, if the data output by an analyte sensor 252 positioned near the mouth of the user or within the facial mask (e.g., in implementations where the user interface 120 is a facial mask) detects the presence of an analyte, the control system 200 can use this data as an indication that the user is breathing through their mouth.

The moisture sensor 254 outputs data that can be stored in the memory device 204 and used by the control system 200. The moisture sensor 254 can be used to detect moisture in various areas surrounding the user (e.g., inside the conduit 140 or the user interface 120, near the user's face, near the connection between the conduit 140 and the user interface 120, near the connection between the conduit 140 and the respiratory therapy device 110, etc.). Thus, in some implementations, the moisture sensor 254 can be coupled to or integrated in the user interface 120 or in the conduit 140 to monitor the humidity of the pressurized air from the respiratory therapy device 110. In other implementations, the moisture sensor 254 is placed near any area where moisture levels need to be monitored. The moisture sensor 254 can also be used to monitor the humidity of the ambient environment surrounding the user, for example, the air inside the bedroom.

The Light Detection and Ranging (LiDAR) sensor 256 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 256 can measure and map an area extending 5 meters or more away from the sensor. The LiDAR data can be fused with point cloud data estimated by an electromagnetic RADAR sensor, for example. The LiDAR sensor(s) 256 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 210 also include a galvanic skin response (GSR) sensor, a blood flow sensor, a respiration sensor, a pulse sensor, a sphygmomanometer sensor, an oximetry sensor, a sonar sensor, a RADAR sensor, a blood glucose sensor, a color sensor, a pH sensor, an air quality sensor, a tilt sensor, a rain sensor, a soil moisture sensor, a water flow sensor, an alcohol sensor, or any combination thereof.

While shown separately in FIG. 1, any combination of the one or more sensors 210 can be integrated in and/or coupled to any one or more of the components of the system 100, including the respiratory therapy device 110, the user interface 120, the conduit 140, the humidifier 160, the control system 200, the user device 260, the activity tracker 270, or any combination thereof. For example, the microphone 220 and the speaker 222 can be integrated in and/or coupled to the user device 260 and the pressure sensor 212 and/or flow rate sensor 132 are integrated in and/or coupled to the respiratory therapy device 110. In some implementations, at least one of the one or more sensors 210 is not coupled to the respiratory therapy device 110, the control system 200, or the user device 260, and is positioned generally adjacent to the user 20 during the sleep session (e.g., positioned on or in contact with a portion of the user 20, worn by the user 20, coupled to or positioned on the nightstand, coupled to the mattress, coupled to the ceiling, etc.).

One or more of the respiratory therapy device 110, the user interface 120, the conduit 140, the display device 150, and the humidifier 160 can contain one or more sensors (e.g., a pressure sensor, a flow rate sensor, or more generally any of the other sensors 210 described herein). These one or more sensors can be used, for example, to measure the air pressure and/or flow rate of pressurized air supplied by the respiratory therapy device 110.

The data from the one or more sensors 210 can be analyzed (e.g., by the control system 200) to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 210, or from other types of data.

The user device 260 (FIG. 1) includes a display device 262. The user device 260 can be, for example, a mobile device such as a smart phone, a tablet, a gaming console, a smart watch, a laptop, or the like. Alternatively, the user device 260 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 262 is generally used to display image(s) including still images, video images, or both. In some implementations, the display device 262 acts as a human-machine interface (HMI) that includes a graphic user interface (GUI) configured to display the image(s) and an input interface. The display device 262 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 260. In some implementations, one or more user devices can be used by and/or included in the system 10.

In some implementations, the system 100 also includes an activity tracker 270. The activity tracker 270 is generally used to aid in generating physiological data associated with the user. The activity tracker 270 can include one or more of the sensors 210 described herein, such as, for example, the motion sensor 138 (e.g., one or more accelerometers and/or gyroscopes), the PPG sensor 154, and/or the ECG sensor 156. The physiological data from the activity tracker 270 can be used to determine, for example, a number of steps, a distance traveled, a number of steps climbed, a duration of physical activity, a type of physical activity, an intensity of physical activity, time spent standing, a respiration rate, an average respiration rate, a resting respiration rate, a maximum heart respiration rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. In some implementations, the activity tracker 270 is coupled (e.g., electronically or physically) to the user device 260.

In some implementations, the activity tracker 270 is a wearable device that can be worn by the user, such as a smartwatch, a wristband, a ring, or a patch. For example, referring to FIG. 2, the activity tracker 270 is worn on a wrist of the user 20. The activity tracker 270 can also be coupled to or integrated a garment or clothing that is worn by the user. Alternatively still, the activity tracker 270 can also be coupled to or integrated in (e.g., within the same housing) the user device 260. More generally, the activity tracker 270 can be communicatively coupled with, or physically integrated in (e.g., within a housing), the control system 200, the memory device 204, the respiratory therapy system 100, and/or the user device 260.

In some implementations, the system 100 also includes a blood pressure device 280. The blood pressure device 280 is generally used to aid in generating cardiovascular data for determining one or more blood pressure measurements associated with the user 20. The blood pressure device 280 can include at least one of the one or more sensors 210 to measure, for example, a systolic blood pressure component and/or a diastolic blood pressure component.

In some implementations, the blood pressure device 280 is a sphygmomanometer including an inflatable cuff that can be worn by the user 20 and a pressure sensor (e.g., the pressure sensor 212 described herein). For example, in the example of FIG. 2, the blood pressure device 280 can be worn on an upper arm of the user 20. In such implementations where the blood pressure device 280 is a sphygmomanometer, the blood pressure device 280 also includes a pump (e.g., a manually operated bulb) for inflating the cuff. In some implementations, the blood pressure device 280 is coupled to the respiratory therapy device 110 of the respiratory therapy system 100, which in turn delivers pressurized air to inflate the cuff. More generally, the blood pressure device 280 can be communicatively coupled with, and/or physically integrated in (e.g., within a housing), the control system 200, the memory device 204, the respiratory therapy system 100, the user device 260, and/or the activity tracker 270.

In other implementations, the blood pressure device 280 is an ambulatory blood pressure monitor communicatively coupled to the respiratory therapy system 100. An ambulatory blood pressure monitor includes a portable recording device attached to a belt or strap worn by the user 20 and an inflatable cuff attached to the portable recording device and worn around an arm of the user 20. The ambulatory blood pressure monitor is configured to measure blood pressure between about every fifteen minutes to about thirty minutes over a 24-hour or a 48-hour period. The ambulatory blood pressure monitor may measure heart rate of the user 20 at the same time. These multiple readings are averaged over the 24-hour period. The ambulatory blood pressure monitor determines any changes in the measured blood pressure and heart rate of the user 20, as well as any distribution and/or trending patterns of the blood pressure and heart rate data during a sleeping period and an awakened period of the user 20. The measured data and statistics may then be communicated to the respiratory therapy system 100.

The blood pressure device 280 may be positioned external to the respiratory therapy system 100, coupled directly or indirectly to the user interface 120, coupled directly or indirectly to a headgear associated with the user interface 120, or inflatably coupled to or about a portion of the user 20. The blood pressure device 280 is generally used to aid in generating physiological data for determining one or more blood pressure measurements associated with a user, for example, a systolic blood pressure component and/or a diastolic blood pressure component. In some implementations, the blood pressure device 280 is a sphygmomanometer including an inflatable cuff that can be worn by a user and a pressure sensor (e.g., the pressure sensor 212 described herein).

In some implementations, the blood pressure device 280 is an invasive device which can continuously monitor arterial blood pressure of the user 20 and take an arterial blood sample on demand for analyzing gas of the arterial blood. In some other implementations, the blood pressure device 280 is a continuous blood pressure monitor, using a radio frequency sensor and capable of measuring blood pressure of the user 20 once very few seconds (e.g., every 3 seconds, every 5 seconds, every 7 seconds, etc.) The radio frequency sensor may use continuous wave, frequency-modulated continuous wave (FMCW with ramp chirp, triangle, sinewave), other schemes such as PSK, FSK etc., pulsed continuous wave, and/or spread in ultra wideband ranges (which may include spreading, PRN codes or impulse systems).

While the control system 200 and the memory device 204 are described and shown in FIG. 1 as being a separate and distinct component of the system 100, in some implementations, the control system 200 and/or the memory device 204 are integrated in the user device 260 and/or the respiratory therapy device 110. Alternatively, in some implementations, the control system 200 or a portion thereof (e.g., the processor 202) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system according to implementations of the present disclosure. For example, a first alternative system includes the control system 200, the memory device 204, and at least one of the one or more sensors 210 and does not include the respiratory therapy system 100. As another example, a second alternative system includes the control system 200, the memory device 204, at least one of the one or more sensors 210, and the user device 260. As yet another example, a third alternative system includes the control system 200, the memory device 204, the respiratory therapy system 100, at least one of the one or more sensors 210, and the user device 260. Thus, various systems can be formed using any portion or portions of the components shown and described herein and/or in combination with one or more other components.

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 262 of the user device 260 (FIG. 1) to manually initiate or terminate the sleep session.

Generally, the sleep session includes any point in time after the user 20 has laid or sat down in the bed 40 (or another area or object on which they intend to sleep), and has turned on the respiratory therapy device 110 and donned the user interface 120. The sleep session can thus include time periods (i) when the user 20 is using the respiratory therapy system 100, but before the user 20 attempts to fall asleep (for example when the user 20 lays in the bed 40 reading a book); (ii) when the user 20 begins trying to fall asleep but is still awake; (iii) when the user 20 is in a light sleep (also referred to as stage 1 and stage 2 of non-rapid eye movement (NREM) sleep); (iv) when the user 20 is in a deep sleep (also referred to as slow-wave sleep, SWS, or stage 3 of NREM sleep); (v) when the user 20 is in rapid eye movement (REM) sleep; (vi) when the user 20 is periodically awake between light sleep, deep sleep, or REM sleep; or (vii) when the user 20 wakes up and does not fall back asleep.

The sleep session is generally defined as ending once the user 20 removes the user interface 120, turns off the respiratory therapy device 110, and gets out of bed 40. In some implementations, the sleep session can include additional periods of time, or can be limited to only some of the above-disclosed time periods. For example, the sleep session can be defined to encompass a period of time beginning when the respiratory therapy device 110 begins supplying the pressurized air to the airway or the user 20, ending when the respiratory therapy device 110 stops supplying the pressurized air to the airway of the user 20, and including some or all of the time points in between, when the user 20 is asleep or awake.

Figure 4:
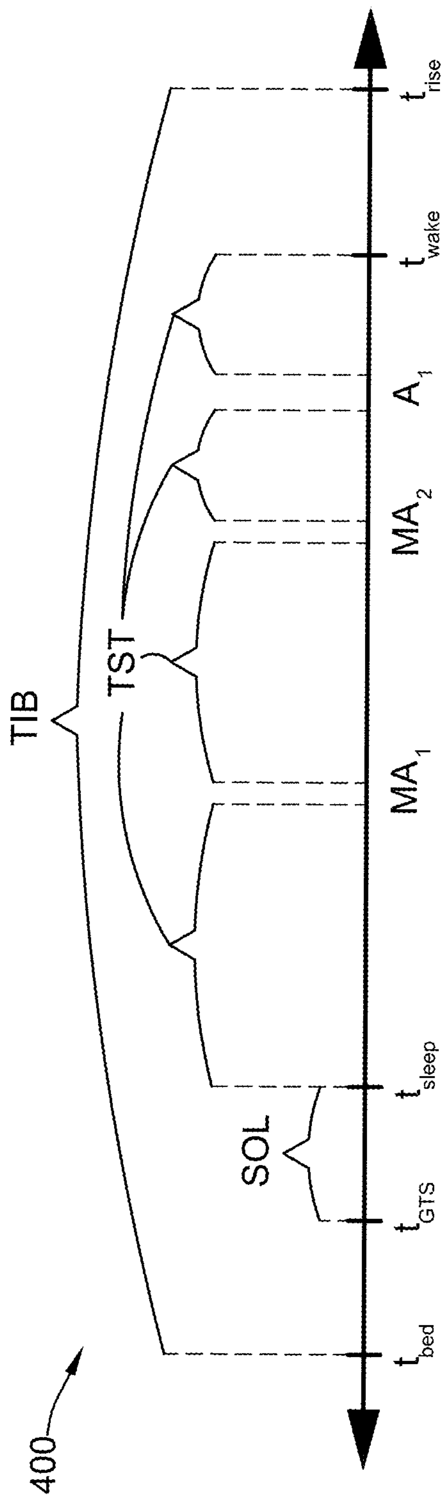
FIG. 4 illustrates an exemplary timeline for a sleep session, according to some implementations of the present disclosure.

Referring to the timeline 400 in FIG. 4 the enter bed time $t_{bed}$ is associated with the time that the user initially enters the bed (e.g., bed 40 in FIG. 2) prior to falling asleep (e.g., when the user lies down or sits in the bed). The enter bed time $t_{bed}$ can be identified based on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 260, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings $MA_1$ and $MA_2$) having a short duration (e.g., 5 seconds, 10 seconds, 30 seconds, 1 minute, etc.) after initially falling asleep. In contrast to the wake-up time $t_{wake}$, the user goes back to sleep after each of the microawakenings $MA_1$ and $MA_2$. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 400 of FIG. 4, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Figure 5:
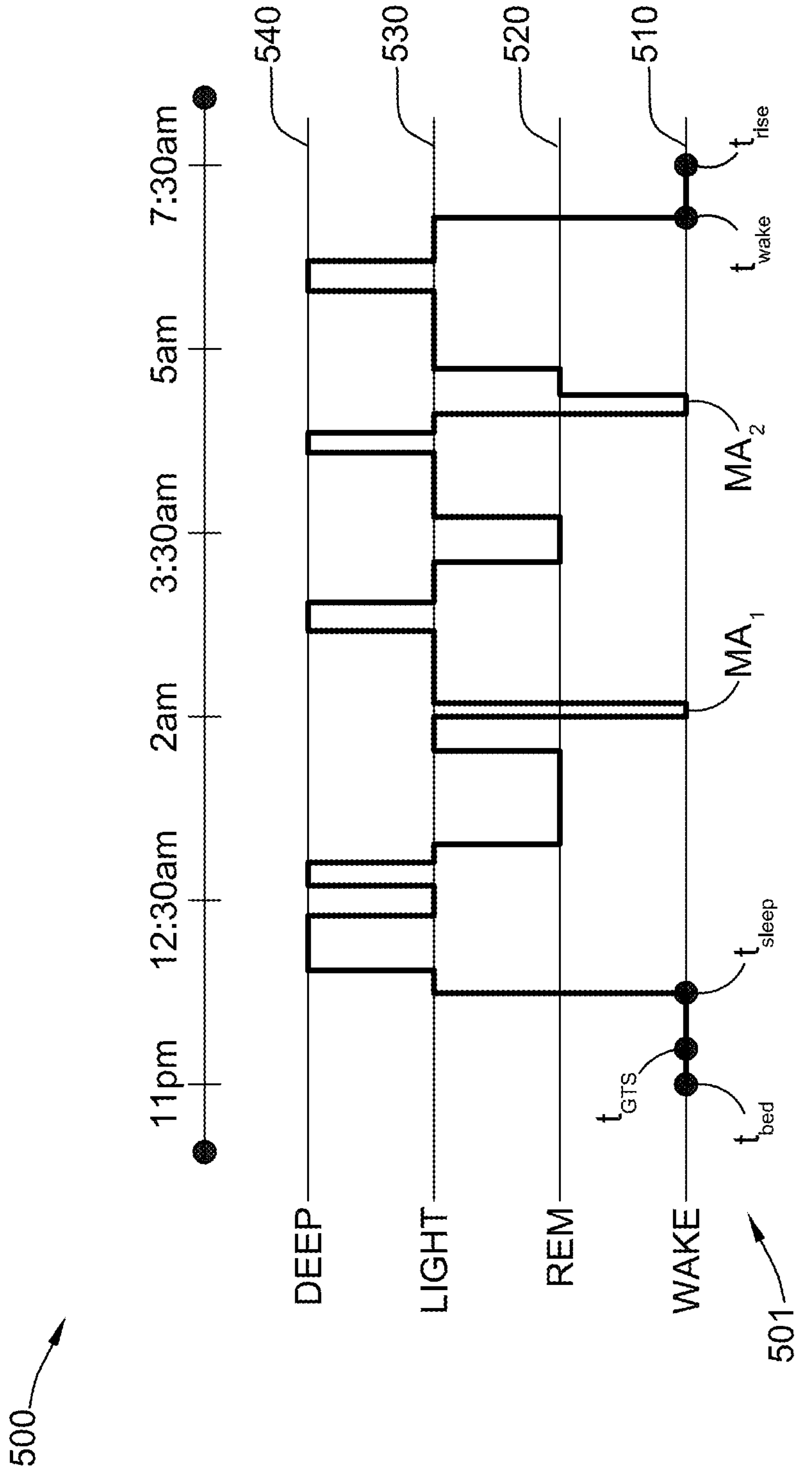
FIG. 5 illustrates an exemplary hypnogram associated with the sleep session of FIG. 4, according to some implementations of the present disclosure.

Referring to FIG. 5, an exemplary hypnogram 500 corresponding to the timeline 400 (FIG. 4), according to some implementations, is illustrated. As shown, the hypnogram 500 includes a sleep-wake signal 501, a wakefulness stage axis 510, a REM stage axis 520, a light sleep stage axis 530, and a deep sleep stage axis 540. The intersection between the sleep-wake signal 501 and one of the axes 510-540 is indicative of the sleep stage at any given time during the sleep session.

The sleep-wake signal 501 can be generated based on physiological data associated with the user (e.g., generated by one or more of the sensors 210 described herein). The sleep-wake signal can be indicative of one or more sleep states, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 500 is shown in FIG. 5 as including the light sleep stage axis 530 and the deep sleep stage axis 540, in some implementations, the hypnogram 500 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration ratio, a number of events per hour, a pattern of events, or any combination thereof. Information describing the sleep-wake signal can be stored in the memory device 204.

The hypnogram 500 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings $MA_1$ and $MA_2$ shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening $MA_1$ and micro-awakening $MA_2$ shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 210 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based on, for example, data generated by the motion sensor 218, the microphone 220, the camera 232, or any combination thereof. The go-to-sleep time can be determined based on, for example, data from the motion sensor 218 (e.g., data indicative of no movement by the user), data from the camera 232 (e.g., data indicative of no movement by the user and/or that the user has turned off the lights) data from the microphone 220 (e.g., data indicative of the user turning off a TV), data from the user device 260 (e.g., data indicative of the user no longer using the user device 260), data from the pressure sensor 212 and/or the flow rate sensor 214 (e.g., data indicative of the user turning on the respiratory therapy device 110, data indicative of the user donning the user interface 120, etc.), or any combination thereof.

In reference back to FIG. 4, there may be an optimum sleep pattern or sleep position for the user from the enter bed time ($t_{bed}$) to the rising time ($t_{rise}$). There also may be an optimum sleep pattern or position between the go-to-sleep time ($t_{GTS}$) and the initial sleep time ($t_{sleep}$) or in response to the micro-awakenings during the sleep session (e.g., the micro-awakenings MA1 and MA2). Further, in reference to FIG. 5, there may similarly be an optimum sleep pattern or sleep position for the user during one or more of the REM, light, and deep stages of sleep. Accordingly, the present application is directed to methods of helping a user (e.g., user 20) achieve these optimum sleep patterns or sleep positions.

Figure 6:
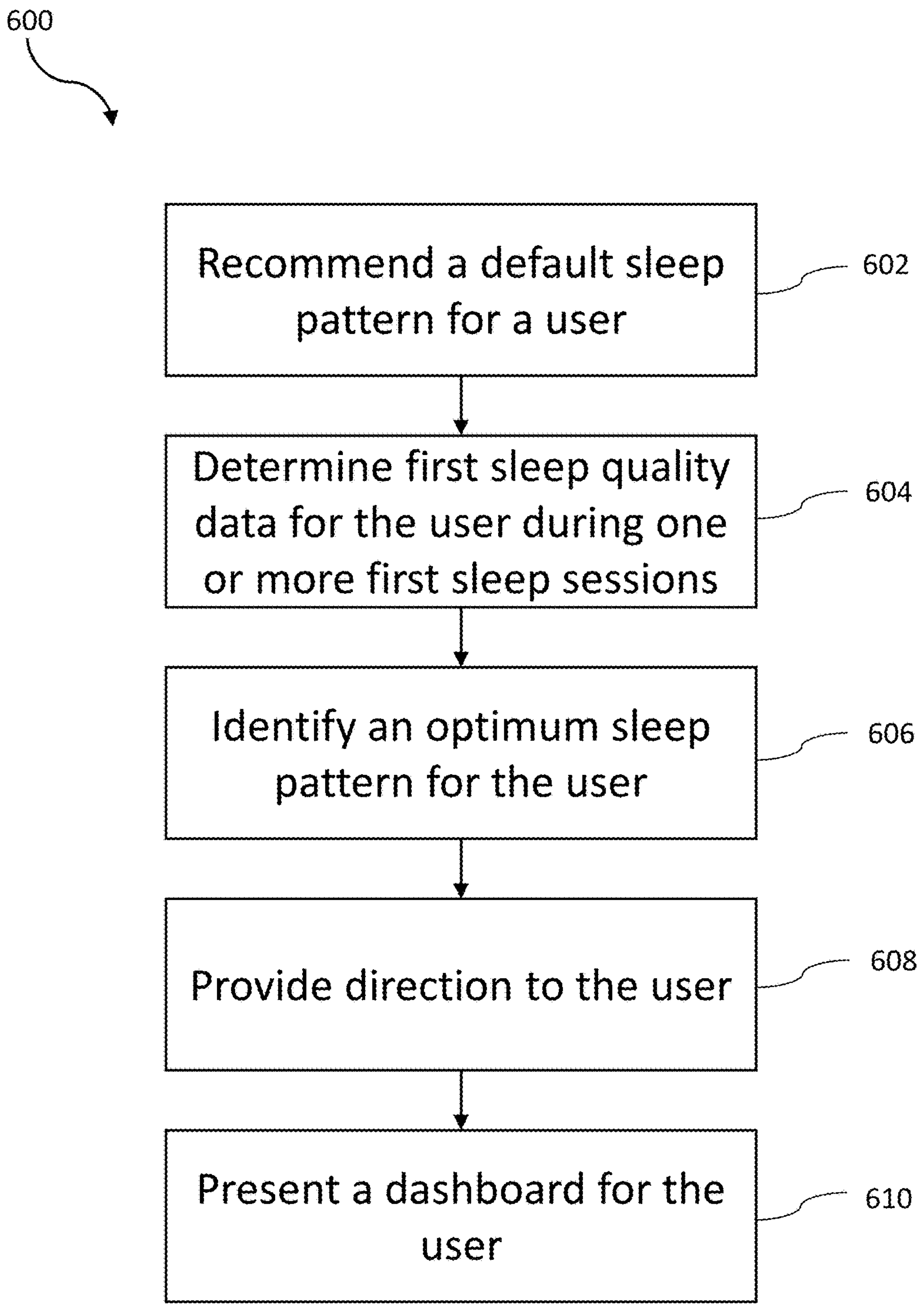
FIG. 6 is a process flow diagram for a method for sleep training according to some implementations of the present disclosure.

Referring to FIG. 6, a method 600 for sleep training according to some implementations of the present disclosure is illustrated. One or more steps of the method 600 can be implemented using any element or aspect of the system 100 described herein.

At step 602, the method 600 includes recommending a default sleep pattern for a user based, at least in part, on crowd-sourced sleep data. According to some aspects, the default sleep pattern can be a series of sleep positions that the user should be in during a period of a sleep session. According to some aspects, the default sleep pattern can simply be a default initial position that the user should be in when the user initiates a sleep session. According to some aspects, the default sleep pattern can be a default predetermined position that the user should maintain for a predetermined period of sleep, not necessarily the initial position when the user initiates the sleep position. According to some aspects, the default sleep pattern can be any combination of the foregoing.

According to some implementations, the default sleep pattern can be determined based on a common sleep pattern among one or more crowd-sourced users associated with the crowd-sourced sleep data who share one or more demographic, medical or physiological traits, or any combination thereof, with the user. For example, the default sleep pattern can be recommended based on the default optimum sleep pattern of a population with demographic and physiological data, such as gender, age, weight, injury (e.g., left arm injury), disease state, health condition, etc., that is similar to the user. Thus, if injury or disease state or health condition is taken into consideration, the default sleep pattern can exclude certain patterns or positions that conflict with the injury or disease state or health condition, such as lying on the stomach for someone who is pregnant.

At step 604, the method 600 includes determining first sleep quality data for the user during one or more first sleep sessions subsequent to the recommending the default sleep pattern and with the user adopting the default sleep pattern in the one or more first sleep sessions. The first sleep quality data indicates the default sleep pattern affects the user's quality of sleep.

According to some implementations, the first sleep quality data correlates historical sleep positions of the user with historical sleep events of the user related to a quality of sleep. The historical sleep events can include, for example, an amount and a type of movement (e.g., such a roll from left-side to supine, supine to prone, etc.), a total amount sleep, an amount of REM sleep, an amount of deep sleep, an amount of light sleep, a length of time to fall asleep, a number of sleep interruptions, an amount of snoring, a number of apnea events, a measure of blood oxygen saturation, or any combination thereof.

At step 606, the method 600 includes identifying based, at least in part, on the first sleep quality data an optimum sleep pattern for the user. The optimum sleep pattern can be identified based, at least in part, on feedback from the user. Similar to the default sleep pattern, and according to some aspects, the optimum sleep pattern can be a series of sleep positions that the user should be in during a period of a sleep session. According to some aspects, the optimum sleep pattern can simply be an initial position that the user should be in when the user initiates a sleep session. According to some aspects, the optimum sleep pattern can be an optimum predetermined position that the user should maintain for a predetermined period of sleep, not necessarily the initial position when the user initiates the sleep position. According to some aspects, the optimum sleep pattern can be any combination of the foregoing.

According to some aspects, the feedback can be information on, for example, the presence of a bed partner, a weather event, a change in one or more medications, use of a drug, use of alcohol, energy level after sleep session, soreness during or after sleep session (e.g., stiff back, more pains, leg cramps, dead arm, etc.), or any combination thereof. According to some implementations, the feedback from the user can be used to override other decisions that may be contrary to the feedback. For example, if a change in sleep pattern is determined to help sleep quality, but the change in sleep pattern conflicts with feedback, the change in sleep pattern may be discarded.

At step 608, the method 600 includes providing direction to the user prior to, during, or any combination thereof one or more second sleep sessions to encourage the user to sleep in the optimum sleep pattern. The direction provided to the user can be one or more mechanical stimulations, one or more aural stimulations, one or more olfactory stimulations, or any combination thereof. The one or more stimulations can be provided to the user effected, at least in part, by one or more devices associated with the user, one or more devices associated with a bed of the user, one or more devices located in an environment of the user, or any combination thereof. According to some implementations, at least one device of the one or more devices associated with the user can be a wearable device, such as user device 260, configured to include specific vibration patterns, with each specific vibration pattern related to a specific sleep position. According to some aspects, every time the user's position changes, the wearable device can detect the change and attempt to correct the position with a vibration. Information from the wearable device can be presented on a dashboard, as disclosed below. In the dashboard, the user can learn about which sleep position(s) give(s) the user the best sleep and lead(s) to the least number of apneas.

Besides a stimulation, the direction can be, for example, instructions for how the user can improve sleep. For example, the instructions can be specific instructions for the user to use a device that can aid in achieving the optimum sleep pattern. Such a device can be, for example, a sleep pillow or a cushion or a mattress that encourages a certain sleep position.

According to some implementations, the direction can be based on an algorithm generated from crowd-sourced direction information. In which case, the method 600 can further include applying reinforcement learning to the algorithm for personalizing the direction specific to the user. The reinforcement learning can be based, at least in part, on which direction is determined to prevent or reduce sleep disordered breathing by the user based on second sleep quality data for the user during the one or more second sleep sessions. Alternatively, or in addition, the reinforcement learning can be based, at least in part, on which direction is determined to not wake the user, a bed partner of the user, or any combination thereof.

At step 610, the method 600 includes presenting a dashboard for the user that communicates how the optimum sleep pattern and the provided direction have affected sleep. The goal for the optimum sleep pattern is for the user to achieve better sleep, such as in the form of less sleep disordered breathing. The dashboard can present information to the user that visually indicates the improvement in the sleep. For example, the dashboard can present information on the number of sleep disordered breathing events before and after the optimum sleep pattern was identified, before and after the direction was provided to the user for achieving the optimum sleep pattern, or a combination thereof. Further, or in the alternative, the dashboard can present information regarding which sleep position, sleep pattern, or any combination thereof provides a fewest number of sleep disordered breathing events.

According to some aspects, the dashboard can further provide guidance to the user throughout the entire process of sleep training, such as throughout the entire process of the method 600. FIGS. 7-10 discussed below show exemplary user interfaces presented by the dashboard throughout the sleep training process and exemplary information that can be presented on the dashboard. However, FIGS. 7-10 are exemplary only and are not meant to limit what information can be shown on the dashboard or limit in any way how the dashboard can appear.

Figure 7:
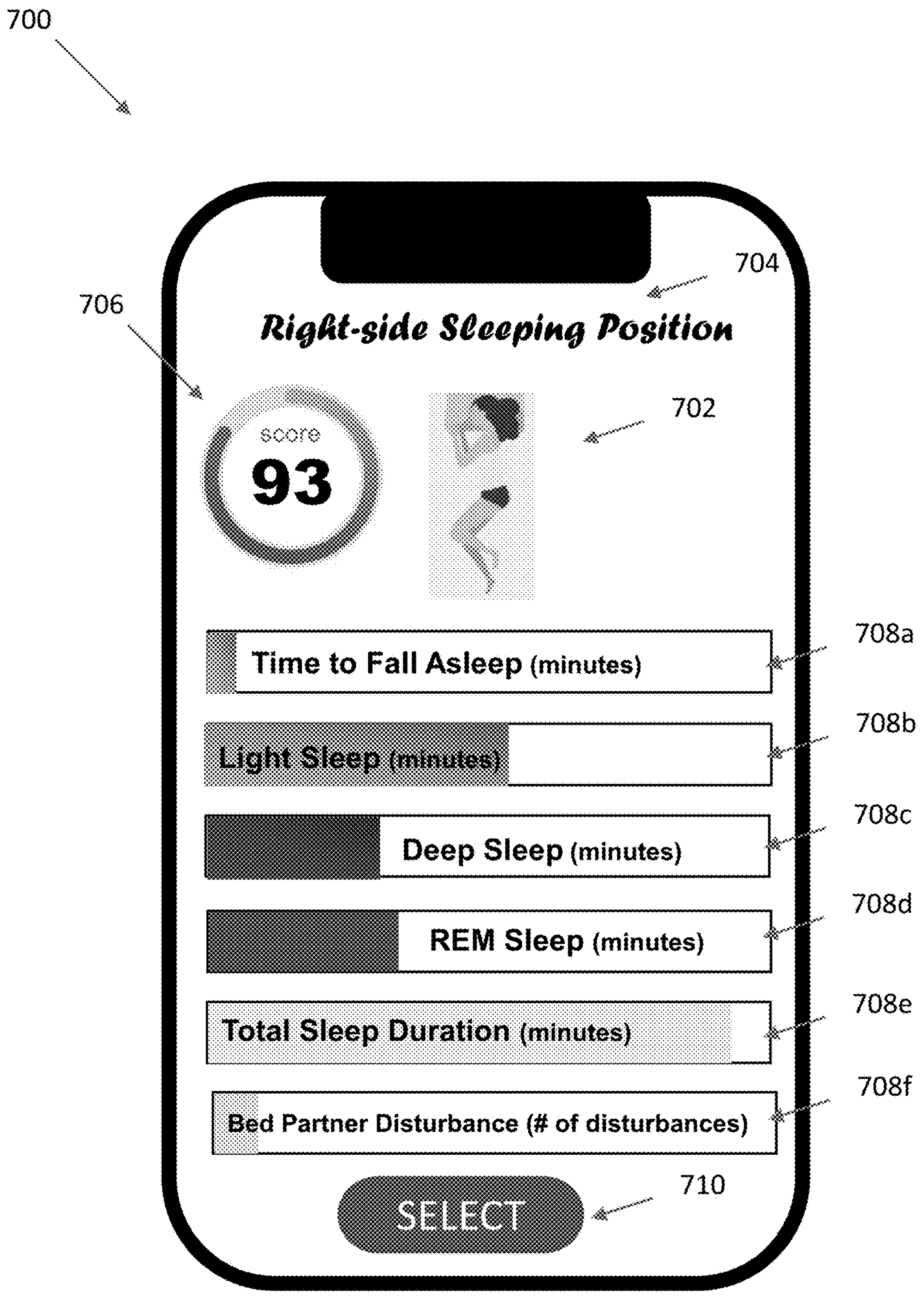
FIG. 7 shows an example of the user interface of a dashboard that can present information related to sleep training, according to aspects of the present disclosure.

Referring to FIG. 7, shown is an example of a user interface 700 of the dashboard, according to aspects of the present disclosure. FIG. 7 specifically shows information on the user being in the "right-side" sleeping position, as represented by the graphic 702 and title 704. Such information can include, for example, an overall sleep score 706 for the sleeping position and various metrics 708*a*-708*f* that quantitatively describe the user's sleep in the sleeping position. Such metrics and the associated graphics can include, for example, time to fall asleep 708*a*; how long the user was in different sleep stages in that sleeping position, such as amount of light sleep 708*b*, amount of deep sleep 708*c*, and amount of REM sleep 708*d*; total sleep duration 708*e* in the position; and the number of bed partner disturbances 708*f*. Thus, the user interface 700 allows a user to understand more aspects on the quality of sleep that the user achieves in the associated sleep position. For example, FIG. 7 shows how long the user slept in the "right-side" sleeping position throughout the night. Presentation of the portion or percentage of time that the user was in that position during a sleep session is informative to user and can be used to confirm efficacy of and encourage sleep habits.

Figure 8:
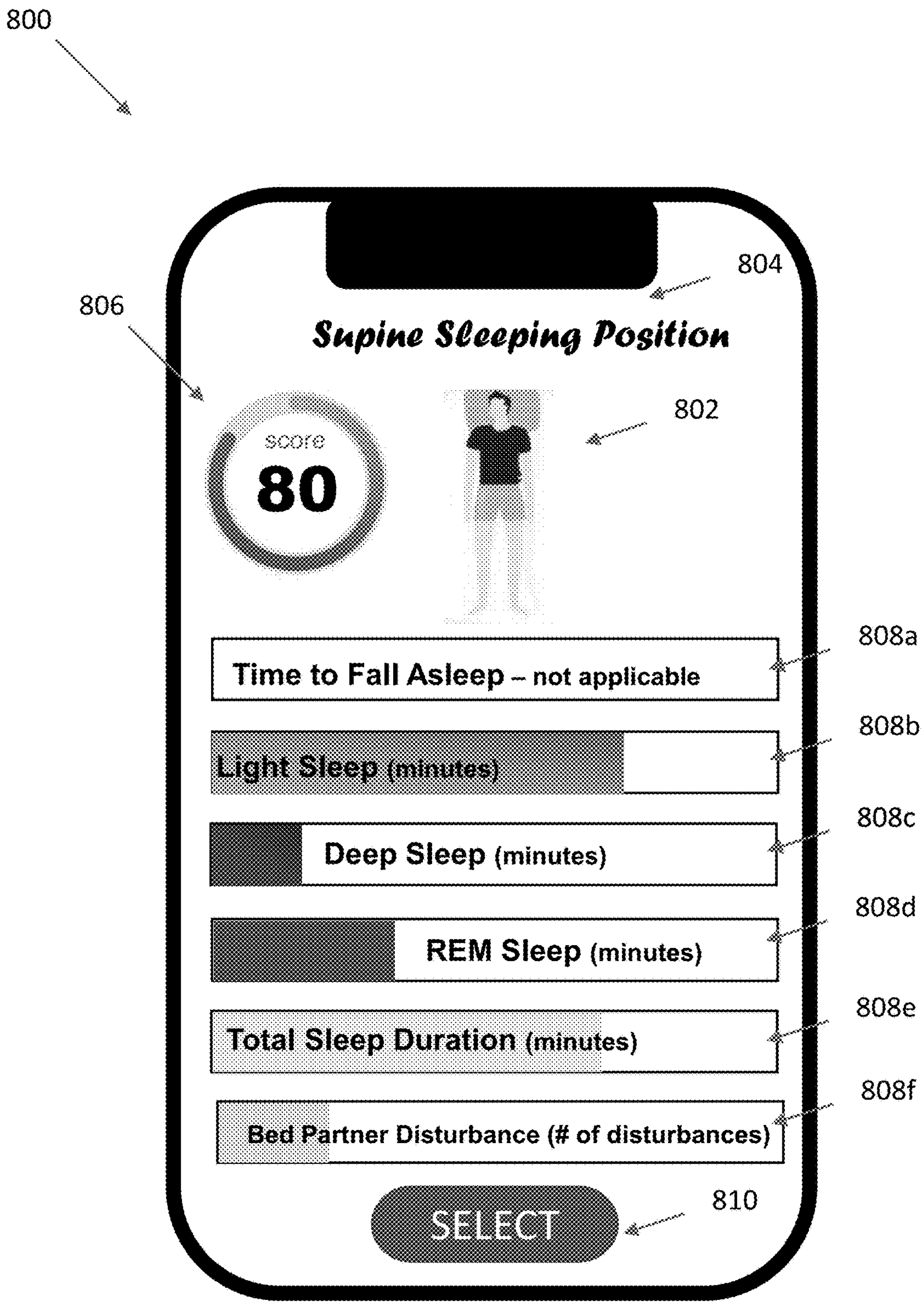
FIG. 8 shows another example of a user interface of the dashboard, according to aspects of the present disclosure.

Referring to FIG. 8, shown is another example of a user interface 800 of the dashboard, according to aspects of the present disclosure. FIG. 8 specifically shows information on the user being in the "supine" sleeping position, as represented by the graphic 802 and title 804. Similar to the description of FIG. 7 above, such information can include, for example, an overall sleep score 806 for the position and various metrics 808*a*-808*f* that quantitatively describe the user's sleep in the sleep position. Such metrics and the associated graphics can include, for example, time to fall asleep 808*a*, amount of light sleep 808*b*, amount of deep sleep 808*c*, amount of REM sleep 808*d*, total sleep duration 808*e*, and number of bed partner disturbances 808*f*. The user interface 800 allows a user to understand more aspects on the quality of sleep that the user achieves in the associated sleep position. Further, based on the similarity in the presentation of the information in the user interface 800 as the user interface 700, the user can easily perceive differences between the two sleep positions.

Although FIGS. 7 and 8 show user interfaces for only two sleep positions, the dashboard can present information on any number of sleep positions assuming by the user during a sleep session. Each user interface for each sleep position can have the same or similar information, such as presented in FIGS. 7 and 8. Alternatively, the user interfaces can present different information. Further, according to some aspects, the user can modify the user interfaces so that the user can control what information (e.g., metrics and associated graphics) is presented in the user interfaces. For example, a user may be more interested in time to fall asleep and bed disturbances rather than time in sleep stages. Such a user may therefore choose to have metrics and associated graphics associated with time to fall asleep and bed disturbances presented on the user interface. The sleep score may similarly be calculated on the time to fall asleep and bed disturbances metrics. Alternatively, the sleep score may be calculated on a predetermined range of metrics whether or not those are presented to the user on the user interface.

Figure 9:
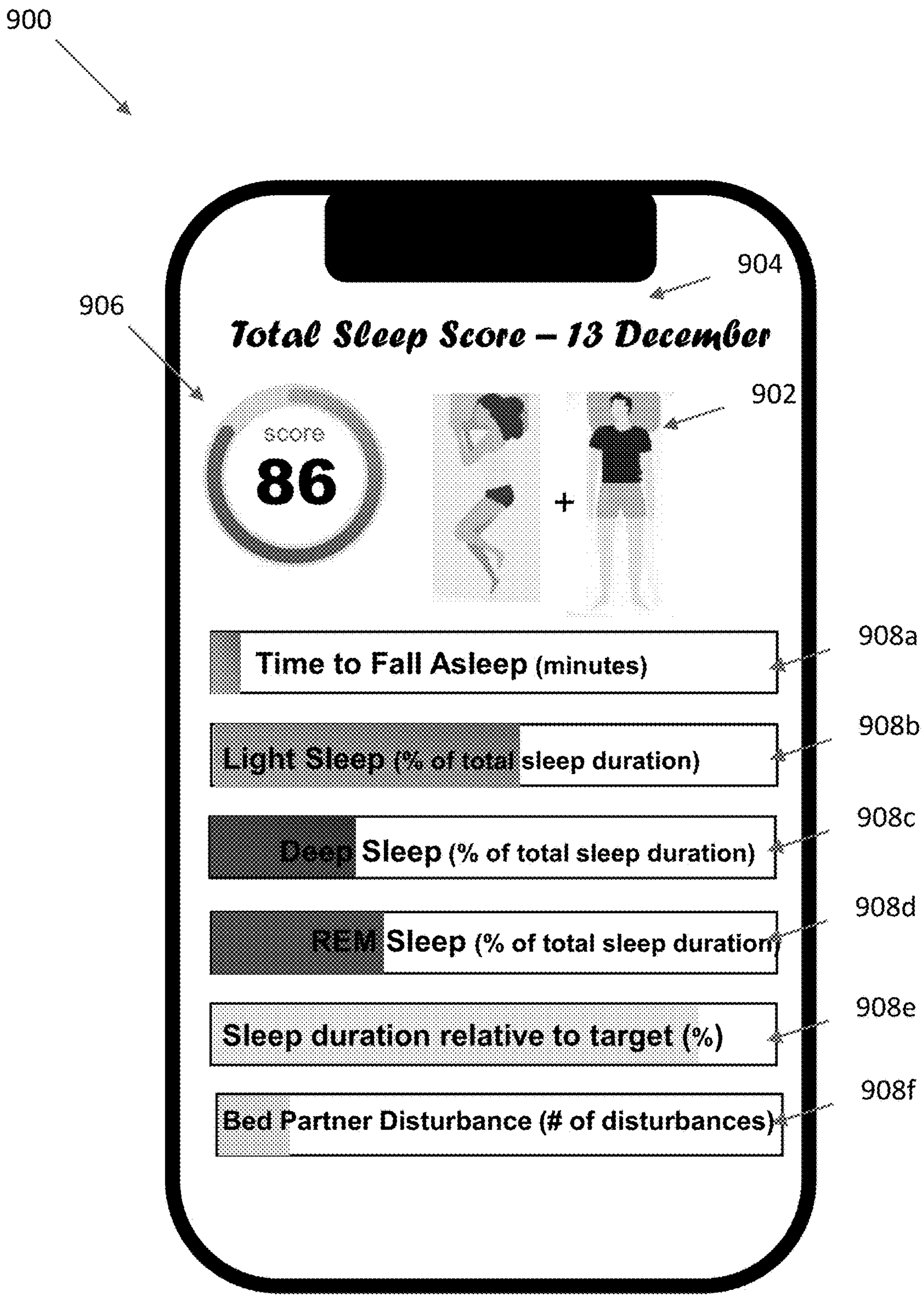
FIG. 9 shows another example of a user interface of the dashboard, according to aspects of the present disclosure.

Referring to FIG. 9, shown is another example of a user interface 900 of the dashboard, according to aspects of the present disclosure. FIG. 9 specifically shows information on the user's sleep score for an entire night (or sleep session), as represented by the graphic 902, title 904, and overall sleep score 906. The overall sleep score 906 is, for example, based on the average sleep score of sleep scores associates with the two sleep positions of the user for an entire night as presented in FIGS. 7 and 8. Similar to FIGS. 7 and 8 above, the information presented to the user in respect of the entire night can include, for example, the time to fall asleep 908*a*. The information can also include the metrics of light sleep 908*b*, deep sleep 908*c*, and REM sleep 908*d* and may be displayed as a percentage of the total sleep duration. Further, the metric 908*e* can be a sleep duration relative to a target sleep duration, rather than the total sleep duration in specific position. The user interface 900 can also include the number of bed partner disturbances 908*f*. The overall sleep score 906 and various metrics 908*a*-908*f* can be understood to quantitatively and/or qualitatively describe the user's (and/or bed partner's) sleep for an entire night based on the sum, average and/or other function of corresponding metrics associates with the user's sleep position(s) during the sleep session.

In addition to the above-described metrics, various other metrics can be shown in the user interfaces 700-900, which include any metric disclosed herein, such as "respiratory events," such as snoring, AHI, wake after sleep onset (WASO); cardiac output; oxygen levels, such as $SpO_2$ levels; movement during sleep/restlessness; amount of snoring; amount of apneas/events/AHI; subjective component, such as user input on when user woke up, presence of child in bed, disturbances to bed partner, environmental conditions such as weather, room temperature, etc., changes in medications, use of drugs/alcohol such as sleeping pill, energy levels after sleep session, and the like.

Figure 10:
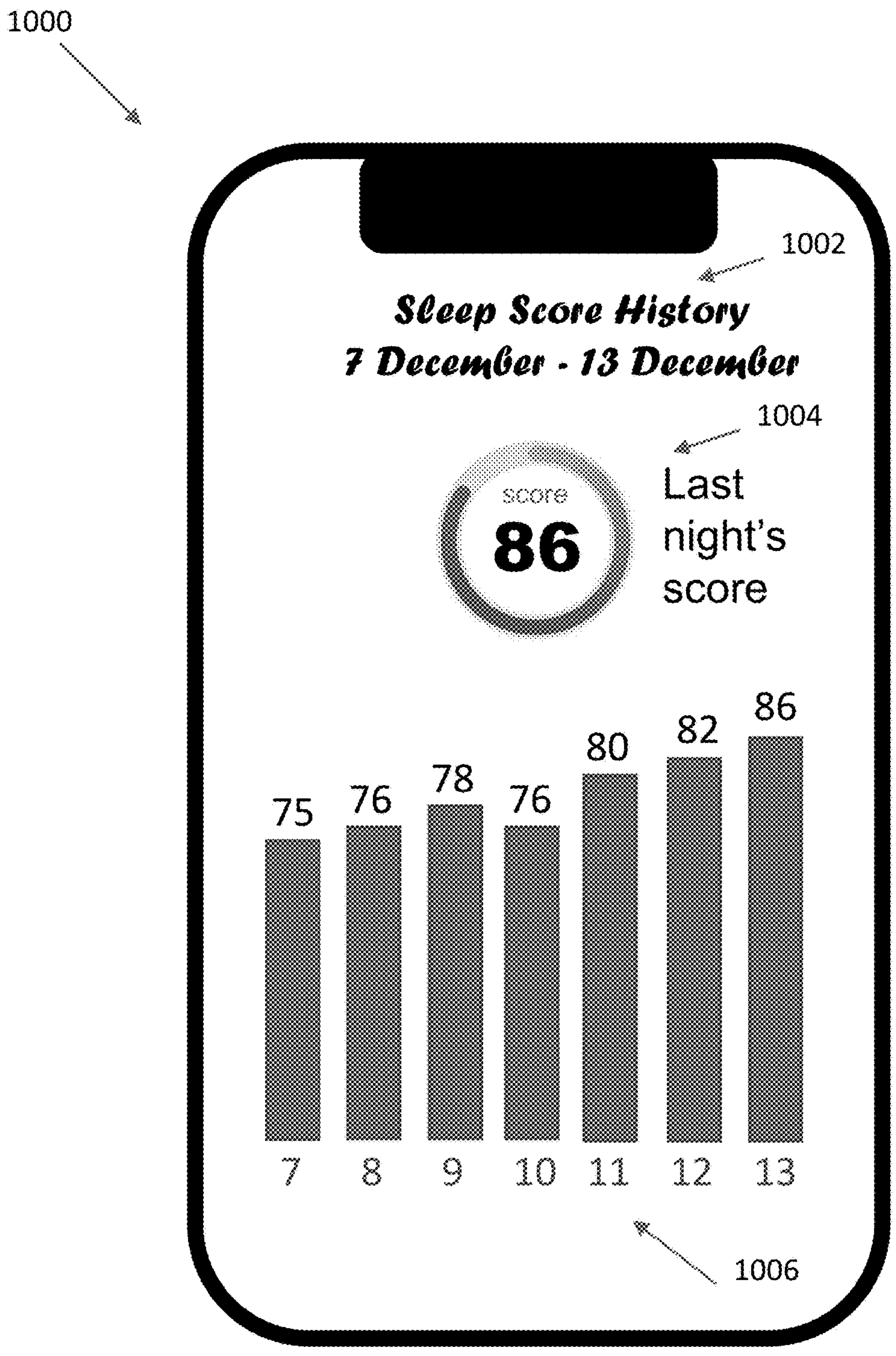
FIG. 10 shows another example of a user interface of the dashboard, according to aspects of the present disclosure.

Referring to FIG. 10, shown is a user interface 1000 showing a summary for a week of sleep, according to aspects of the present disclosure. For example, the title 1002 indicates what days the presented information is for. The score 1004 indicates the sleep score for the previous night. Alternatively, the score 1004 can be the sleep score for the entire seven-day period shown in the user interface 1000. The plot 1006 can show various representations of the sleep scores for the nights presented in the user interface 1000, in the illustrated case being December 7 through December 13. The user interface 1000 helps visualize for the user how the quality of sleep has improved (or stayed the same or declined) since initiating the sleep training discussed above with respect to the method 600.

As described above, the present disclosure provides systems and methods for training a user to sleep in an optimum sleep pattern during sleep. According to some aspects, the user may select a sleeping position that gives the user the most optimum sleep quality or a desired outcome (such as in the form of lowest bed partner sleep disturbance, shortest sleep onset latency, etc.). The dashboard may optionally include a "SELECT" button 710, 810 as shown in FIGS. 7 and 8 which allows the user to choose the preferred sleeping position. For example, the user may prefer to spend more time on the "right-side" sleeping position as the "right-side" sleeping position provides a higher overall sleep score relative to the "supine" sleeping position. Upon clicking the "SELECT" button 710, a direction may be provided to the user prior to, during, or any combination thereof one or more second sleep sessions to encourage the user to sleep in the selected sleeping position.

One or more elements or aspects or steps, or any portion (s) thereof, from one or more of any of claims 1 to 19 below can be combined with one or more elements or aspects or steps, or any portion(s) thereof, from one or more of any of the other claims 1 to 19 or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method for sleep training a user of a respiratory therapy system, the method comprising:

providing the respiratory therapy system configured to deliver pressurized air to the user during sleep and to generate respiratory therapy data indicative of at least one sleep disordered breathing metric;

recommending a default sleep pattern for the user based, at least in part, on crowd-sourced sleep data;

responsive to the user adopting the recommended default sleep pattern, determining first sleep quality data for the user during a first sleep session, the first sleep quality data being determined at least in part from the respiratory therapy data generated by the respiratory therapy system during the first sleep session and including the at least one sleep disordered breathing metric;

determining based, at least in part, on the first sleep quality data an optimum sleep pattern for the user that reduces the at least one sleep disordered breathing metric relative to the default sleep pattern; and during a second sleep session, delivering a mechanical stimulation to the user via a wearable device to encourage the user to sleep in the optimum sleep pattern, the wearable device detecting a change in sleep position of the user and delivering the mechanical stimulation in response to detecting the change in sleep position, the mechanical stimulation comprising a specific vibration pattern related to the sleep position of the user and selected to induce a change in the user's sleep position toward the optimum sleep pattern while maintaining the user asleep.

2. The method of claim 1, the method further comprising subsequent to the first and second sleep sessions, presenting a dashboard to the user that indicates how the optimum sleep pattern and the providing the direction have affected impacted sleep of the user, wherein the direction is based on an algorithm generated from crowd-sourced direction information; and applying reinforcement learning to the algorithm for personalizing the direction specific to the user.

3. The method of claim 2, wherein the reinforcement learning is based, at least in part, on which direction is determined to prevent or reduce sleep disordered breathing by the user based on second sleep quality data for the user during the second sleep session.

4. The method of claim 2, wherein the reinforcement learning is based, at least in part, on which direction is determined to not wake the user, a bed partner of the user, or any combination thereof.

5. The method of claim 1, wherein the first sleep quality data correlates historical sleep positions of the user with historical sleep events of the user related to a quality of sleep.

6. The method of claim 5, wherein the historical sleep events include an amount and a type of movement, a total amount sleep, an amount of REM sleep, an amount of deep sleep, an amount of light sleep, a length of time to fall asleep, a number of sleep interruptions, an amount of snoring, a number of apnea events, a measure of blood oxygen saturation, or any combination thereof.

7. The method of claim 1, wherein the default sleep pattern is determined based on a common sleep pattern among one or more crowd-sourced users associated with the crowd-sourced sleep data who share one or more demographic, medical or physiological traits, or any combination thereof, with the user.

8. The method of claim 2, further comprising presenting information on the dashboard regarding which sleep position, sleep pattern, or any combination thereof provides a fewest number of sleep disordered breathing events.

9. The method of claim 2, wherein the direction further includes one or more aural stimulations, one or more olfactory stimulations, or any combination mechanical, aural, or olfactory provided to the user effected, at least in part, by the wearable device and one or more devices associated with the user, one or more devices associated with a bed of the user, one or more devices located in an environment of the user, or any combination thereof.

10. The method of claim 1, wherein the optimum sleep pattern is identified determined based, at least in part, on feedback from the user.

11. The method of claim 10, wherein the feedback provides information on presence of a bed partner, a weather event, a change in one or more medications, use of a drug, use of alcohol, energy level after sleep session, soreness during or after sleep session, or any combination thereof.

12. The method of claim 1, wherein the default sleep pattern is a default sleep position, a default initial position, a default predetermined position which the user should maintain for a predetermined period of sleep, or a combination of positions during sleep.

13. The method of claim 1, wherein the optimum sleep pattern is an optimum sleep position, an optimum initial position, an optimum predetermined position which the user should maintain for a predetermined period of sleep, or a combination of positions during sleep.

14. The method of claim 2, wherein the direction includes instructions to use a device to encourage a certain sleep position.

15. A system comprising:
- a control system comprising one or more processors; and
- a memory having stored thereon machine readable instructions;
- wherein the control system is coupled to the memory, and the method of claim 1 is implemented when the machine executable instructions in the memory are executed by at least one of the one or more processors of the control system.

16. A system for sleep training, the system comprising a control system configured to implement the method of claim 1.

17. A non-transitory computer readable storage medium comprising instructions which, when executed by a computer, cause the computer to carry out the method of claim 1.

18. A method for sleep training a user of a respiratory therapy system, the method comprising:
- providing the respiratory therapy system configured to deliver pressurized air to the user via a patient interface during sleep and to generate respiratory therapy data indicative of breath flow, pressure, and usage;
- recommending, by a control system comprising one or more processors, a default sleep pattern for the user based, at least in part, on crowd-sourced sleep data;
- responsive to the user adopting the recommended default sleep pattern, determining, by the control system, first sleep quality data for the user during a first sleep session, the first sleep quality data being determined at least in part from the respiratory therapy data generated by the respiratory therapy system during the first sleep session;
- determining, by the control system and based, at least in part, on the first sleep quality data an optimum sleep pattern for the user;
- during a second sleep session, operating, by the control system, a closed-loop positional-therapy control algorithm that:
  - continuously receives, from a wearable device worn by the user, position data indicative of a current sleep position of the user,
  - compares the current sleep position to the optimum sleep pattern, and
  - when the current sleep position is determined not to conform to the optimum sleep pattern, causes the wearable device to deliver a mechanical stimulation to the user according to a specific vibration pattern related to the current sleep position to induce the user to change sleep position toward the optimum sleep pattern while minimizing arousal of the user.

19. The method of claim 18, wherein the first sleep quality data comprises respiratory therapy data correlated with sleep position data for the user during the first sleep session, and wherein the respiratory therapy data includes one or more of breath flow, pressure, snoring, apnea events, mask leak, or blood oxygen saturation.

20. The method of claim 18, wherein the specific vibration pattern is selected from a plurality of specific vibration patterns based on the current sleep position of the user, each of the plurality of specific vibration patterns being related to a respective sleep position.

* * * * *